United States Patent
Dong et al.

(10) Patent No.: US 11,528,928 B2
(45) Date of Patent: Dec. 20, 2022

(54) COMPOSITION COMPRISING SIALLYLACTOSE FOR USE IN ENHANCING LEARNING SKILLS AND MEMORY FUNCTION

(71) Applicant: NESTEC S.A., Vevey (CH)

(72) Inventors: Zhizhong Dong, Beijing (CN); Yujie Shi, Beijing (CN); Bing Wang, New South Wales (AU)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/558,339

(22) PCT Filed: Mar. 17, 2016

(86) PCT No.: PCT/EP2016/055890
§ 371 (c)(1),
(2) Date: Sep. 14, 2017

(87) PCT Pub. No.: WO2016/146789
PCT Pub. Date: Sep. 22, 2016

(65) Prior Publication Data
US 2018/0064152 A1 Mar. 8, 2018

(30) Foreign Application Priority Data
Mar. 18, 2015 (WO) ................ PCT/CN2015/074457

(51) Int. Cl.
*A23L 33/10* (2016.01)
*A23L 33/00* (2016.01)
*C07H 3/04* (2006.01)
*C07H 5/04* (2006.01)

(52) U.S. Cl.
CPC ............... *A23L 33/10* (2016.08); *A23L 33/40* (2016.08); *C07H 3/04* (2013.01); *C07H 5/04* (2013.01); *A23V 2002/00* (2013.01)

(58) Field of Classification Search
CPC ........... A23L 33/10; A23L 33/40; C07H 3/04; C07H 5/04; A23V 2002/00
USPC .......................... 426/531, 580, 587, 588, 801
See application file for complete search history.

(56) References Cited

U.S. PATENT DOCUMENTS

| 2003/0060445 A1 | 3/2003 | Wilson |
| 2004/0202765 A1 | 10/2004 | McMahon et al. |
| 2006/0247153 A1 | 11/2006 | McMahon et al. |
| 2010/0233129 A1* | 9/2010 | Fichot .................. A61K 31/351 424/93.4 |
| 2013/0137643 A1 | 5/2013 | Zimmer et al. |
| 2015/0305384 A1 | 10/2015 | Chichlowski et al. |

FOREIGN PATENT DOCUMENTS

| EP | 2880993 | 6/2015 |
| WO | 2013057049 | 4/2013 |

OTHER PUBLICATIONS

Williams et al., "The impact of otitis media on cognitive and educational outcomes", Nov. 2, 2009, MJA, vol. 191 No. 9, pp. S69-S72. (Year: 2009).*
"Recurrent Middle Ear Infections Can Have A Major Impact On Children's Development" Feb. 6, 2007, https://www.sciencedaily.com/releases/2007/02/070205115128.htm, pp. 1-2. (Year: 2007).*
"Childhood Infections Stunt Growth, Shorten Life", Science Daily, 2005, https://www.sciencedaily.com/releases/2005/12/051227102639.htm, pp. 1-2. (Year: 2005).*
Sakai et al. "Effects of Feeding Sialyllactose and Galactosylated N-AcetyineuraminicAcid on Swimming Learning Ability and Brain Lipid Composition in Adult Rats" J. Appl. Glycosci., 2006, vol. 53, pp. 249-254.
Jacobi et al. "Dietary Isomers of Sialyllactose increase Ganglioside Sialic Acid Concentrations in the Corpus Callosum and Cerebellum and Modulate the Colonic Microbiota of Formula-Fed Piglets" The Journal of Nutrition, 2016, vol. 146, pp. 200-208.
Wang, Bing "Sialic Acid is an Essential Nutrient for Brain Development and Cognition" Annual Review of Nutrition, 2009, vol. 29, pp. 177-222.
Karim, "Is Sialic Acid in Milk Food for the Brain?", Cab Reviews: Perspectives in Agriculture, Veterinary Science, Nutrition and Natural Resources, 1(018), Jun. 1, 2006, XP055589276.
China Patent Office Action Received for Application No. 201680013894.5, dated Jul. 14, 2020, 22 Pages.
Shao et al., "Fetal and Neonatal Brain Injury", Shanghai Science and Technology Education Press, 1st edition, Jan. 2008, pp. 462-466.
Jiang et al., "Untie the Bird's Nest Password", Guangdong Map Publishing House, 1st edition, Jan. 31, 2014, pp. 58-63.

* cited by examiner

Primary Examiner — Leslie A Wong
(74) Attorney, Agent, or Firm — K&L Gates LLP

(57) ABSTRACT

This invention relates to the use of a nutritional composition comprising sialylated oligosaccharides for enhancing cognitive development and learning skills in mammals. The nutritional composition comprises 3'-Siallylactose (3'-SL) and 6'-Siallylactose (6'-SL) in a weight ratio between 10:1 and 1:10 and is specifically for use in enhancing learning skills and/or enhancing memory function in an individual by increasing the sialic acid (Neu5Ac) concentration in the brain of said individual.

16 Claims, 9 Drawing Sheets

FIG. 8

| Treatment | Learning speed | Memory | | sialic acid content in frontal cortex | sialic acid content in hippocampus |
|---|---|---|---|---|---|
| | | short term memory(STM) | Long-term memory (LTM) | | |
| Sialyl core 1 (cGMP) | N | N | N | N/A | N/A |
| Sialyllactose | Yes (Faster in both easy and difficult task) | Yes (Difficult task) | Yes (Easy task) | Increased total Neu5Ac and gangliosides bound form Neu5Ac | Increased total Neu5Ac and gangliosides bound form Neu5Ac |
| Sialyllactose/ Sialyl core 1/ lactoferrin | N | N | N | N/A | N/A |

COMPOSITION COMPRISING SIALLYLACTOSE FOR USE IN ENHANCING LEARNING SKILLS AND MEMORY FUNCTION

CROSS REFERENCE TO RELATED APPLICATIONS

The present application is a National Stage of International Application No. PCT/EP2016/055890, filed on Mar. 17, 2016, which claims priority to International Application No. PCT/CN2015/074457, filed on Mar. 18, 2015, the entire contents of which are being incorporated herein by reference.

FIELD OF THE INVENTION

This invention relates to a nutritional composition comprising 3'-Siallylactose (3'-SL) and 6'-Siallylactose (6'-SL) and to the use of said composition for enhancing learning skills and memory function in an individual. This enhancement is particularly achieved by the nutritional composition of the invention by increasing the sialic acid (Neu5Ac) concentration in the brain and/or enhancing neuroplasticity in the brain of said individual.

BACKGROUND OF THE INVENTION

The early stages of neurodevelopment in infants are crucial for establishing neural structures and synaptic connections that influence brain biochemistry well later in life, including adulthood. This postnatal period of rapid neural growth is of critical importance for cell migration, neurite outgrowth, synaptic plasticity, and axon fasciculation. These processes thus place an unusually high demand on the intracellular pool of nutrients and biochemical precursors. Therefore, early nutrition can affect brain structure and function permanently.

Breast milk is usually referred to as the optimal source of nutrition for the early stage of human life, as it provides all the necessary nutrients for normal growth and development. It consists of nutrients, such as proteins, lipids, carbohydrates, minerals, vitamins, and trace elements that babies need to grow healthy. It also contains immune-related components such as IgA, leukocytes, oligosaccharides, lysozyme, lactoferrin, interferon-γ, nucleotides, cytokines, and others. Several of these compounds offer passive protection in the gastrointestinal tract and to some extent in the upper respiratory tract, preventing adherence of pathogens to the mucosa and thereby protecting the breast-fed infant against invasive infections. Human milk also contains essential fatty acids, enzymes, hormones, growth factors, polyamines, and other biologically active compounds, which may play an important role in the health benefits associated with breast-feeding.

However, in some cases breast feeding is inadequate or unsuccessful or inadvisable for medical reasons or the mother chooses not to breast feed either at all or for a period of more than a few weeks. Infant feeding formulas have been developed for these situations. Today, infant formulas are commonly used to provide a supplemental source or the sole source of nutrition in early life. They may be used instead of or in addition to breast milk. Consequently, infant formulas are often designed to resemble breast milk as closely as possible in terms of composition and function. Milk fortifiers (including human milk fortifiers) and supplements have also been developed to provide specific health benefits to infants, especially those who require particular needs such as the preterm infants, the small for gestational age (SGA) infants and/or the low birth weight (LBW) infants.

Recently, evidence is accumulating that breastfeeding may provide long-term cognitive advantages over formulae feeding. However, the underlying mechanism to explain the relationship between breastfeeding and cognitive development remains unclear.

Human milk is known to be particularly rich in lactose based oligosaccharides. These generally non-digestible oligosaccharides are extensions of the milk sugar lactose brought about by the action of a series of glycosyltransferases such as those transferring N-acetyl-glucosamine, galactose, sialic acid or fucose.

Lastly, sialic acids have been suggested to play important roles in the development of infant brain (Wang et al. 1998; Comparative Biochemistry and Physiology Part A: Molecular & Integrative Physiology, Vol. 119, 435-439). Previously, Morgan et al. found that intraperitoneal injection of N-acetylneuraminic acid as a single ingredient enhances learning speed in adult rats and suggest that the brain concentration of N-acetylneuraminic acid has an effect on behavior (Morgan et al. 1980, Journal of Nutrition, Vol. 110, 416-424). Further, learning and memory functions were proposed to be promoted by supplementation with protein-bound sialic acid in the form of dietary CGMP (Casein glycomacropeptide) as a single ingredient (Wang et al., 2007, American Journal of Clinical Nutrition, Vol. 85, No. 2, 561-569).

Sialic acid (Sia) is a family of 9-carbon sugar acids, which occurs in large amounts in human milk oligosaccharides and is an essential component of brain gangliosides and sialylated glycoproteins, particularly as precursors for the synthesis of the polysialic acid (polySia) glycan that post-translationally modify the cell membrane-associated neural cell adhesion molecules (NCAM).

Neonates have limited capacity for de novo endogenous synthesis of sialic acid, while human breast milk is noteworthy in containing exceptionally high levels of sialic acid glycoconjugates. The predominant form of sialic acid in human breast milk is N-acetylneuraminic acid (Neu5Ac). Sialic acid may thus be a conditional nutrient during periods of rapid brain growth. Nevertheless, common infant formulae provide little or no sialic acid (0~0.2 g/L) as compared with mature human breast milk (~0.7 g/L).

Therefore, a need still exists to provide optimal nutritional support for developing brains, such as an improved nutritional composition for use in promoting brain development, keeping in mind that brain is a very complex organ with many areas.

In particular, there is still a need to provide an improved nutritional composition that may enhance learning skills and particularly learning speed in an individual, such as in an infant.

Further, there is a need to provide an improved nutritional composition that may enhance memory function in an individual, and preferably of both, short-term memory function and long-term memory function.

Moreover, there is still a need for providing an improved nutritional composition for use in enhancing functions of perception, motor control, self-awareness, cognitive functioning and/or interpersonal experience in an individual.

These needs are met by the subject-matter of the present invention as disclosed below.

SUMMARY OF THE INVENTION

The present inventors surprisingly found that providing an individual with sialylated oligosaccharides in the form of sialyllactose may specifically enhance learning skills and memory function in an individual by increasing the sialic acid (Neu5Ac) concentration in the brain of said individual, particularly in the hippocampus and/or the frontal cortex of said individual. The sialic acid increase in this/these specific body part(s) can be seen as a new way of treatment which, in turn, opens a new clinical field.

Accordingly, in a first aspect, the present invention provides a nutritional composition comprising 3'-Siallylactose (3'-SL) and 6'-Siallylactose (6'-SL) in a weight ratio between 10:1 and 1:10 for use in enhancing learning skills and/or enhancing memory function in an individual, especially by increasing the sialic acid (Neu5Ac) concentration in the brain of said individual.

In a preferred embodiment of this nutritional composition, 3'-Siallylactose (3'-SL) and 6'-Siallylactose (6'-SL) are comprised in a weight ratio between 10:1 and 2:1, preferably between 8:1 and 3:1, between 6:1 and 3:1, between 5:1 and 3:1, between 5:1 and 4:1, or between 4.7:1 and 4.1:1, and most preferably in a ratio of 4.4:1.

In another preferred embodiment of this nutritional composition, 3'-Siallylactose (3'-SL) and 6'-Siallylactose (6'-SL) are comprised in a weight ratio between 6:1 and 1:10, preferably between 5.9:1 and 1.5:10, more preferably between 5.86:1 and 1.53:10, and most preferably in a ratio of 1:1.

In a particular embodiment of the first aspect, 3'-Sialyllactose (3'-SL) and 6'-Siallylactose (6'-SL) are comprised in the nutritional composition of the first aspect in an amount of from 50 mg to 2500 mg of total sialyllactose per L of the nutritional composition, preferably from 60 mg to 2000 mg of total sialyllactose per L of the nutritional composition, more preferably from 80 mg to 1000 mg of total sialyllactose per L of the nutritional composition and most preferably from 87.5 mg to 735 mg of total sialyllactose per L of the nutritional composition.

In a specific embodiment of the first aspect, the nutritional composition is administered to the individual during the early age of said individual, and preferably during the infant phase of said individual.

It is further preferred that the nutritional composition is administered to the individual during the first 12 months after birth, during the first 8 months after birth, or during the first 6 months after birth, and more preferably during the first 4 months after birth, or during the first 2 months after birth.

In another particular embodiment of the first aspect, 3'-Siallylactose (3'-SL) and 6'-Siallylactose (6'-SL) are administered to the individual in an amount effective to provide from 110 mg to 180 mg, preferably from 120 mg to 170 mg, more preferably from 125 mg to 165 mg of total sialyllactose per kg body weight per day, and most preferably in an amount effective to provide 131 mg or 162 mg of total sialyllactose per kg body weight per day.

It is preferred that 3'-Siallylactose (3'-SL) and 6'-Siallylactose (6'-SL) are administered to the individual during the first two weeks after birth in an amount effective to provide from 140 mg to 180 mg, preferably from 150 mg to 170 mg, more preferably from 160 mg to 165 mg and most preferably 162 mg of total sialyllactose per kg body weight per day, It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth in an amount effective to provide from 110 mg to 150 mg, preferably from 120 mg to 140 mg, more preferably from 125 mg to 135 mg and most preferably 131 mg of total sialyllactose per kg body weight per day.

In yet another particular embodiment of the nutritional composition of the first aspect, 3'-Siallylactose (3'-SL) and 6'-Siallylactose (6'-SL) are administered to the individual in an amount corresponding to from 350 mg to 530 mg, preferably from 380 mg to 500 mg, more preferably from 390 mg to 490 mg of N-Acetyl-neuraminic acid (Neu5Ac) per kg body weight per day, and most preferably in an amount corresponding to 393 mg or 487 mg of N-Acetyl-neuraminic acid (Neu5Ac) per kg body weight per day.

It is preferred that 3'-Siallylactose (3'-SL) and 6'-Siallylactose (6'-SL) are administered to the individual during the first two weeks after birth in an amount corresponding to from 450 mg to 530 mg, preferably to from 480 mg to 500 mg, more preferably to from 485 mg to 490 mg and most preferably to 487 mg of N-Acetyl-neuraminic acid (Neu5Ac) per kg body weight per day.

It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide from 350 mg to 430 mg, preferably from 380 mg to 400 mg, more preferably from 390 mg to 395 mg and most preferably 393 mg of N-Acetyl-neuraminic acid (Neu5Ac) per kg body weight per day.

In another preferred embodiment of the first aspect, increasing the sialic acid (Neu5Ac) concentration in the brain of the individual comprises increasing the sialic acid (Neu5Ac) concentration in a brain region selected from hippocampus, frontal cortex, or a combination thereof, and preferably selected from hippocampus.

In a further preferred embodiment of the first aspect, the use in enhancing memory function of an individual comprises enhancing long-term memory function.

In a further preferred embodiment of the first aspect, the use in enhancing memory function of an individual comprises enhancing short-term memory function.

In a further preferred embodiment of the first aspect, the use in enhancing memory function of an individual comprises enhancing both, short-term memory function and long-term memory function In another preferred embodiment of the first aspect, the individual is a mammal, more preferably a pet or a human, and most preferably a human.

In yet another preferred embodiment of the first aspect, the individual is selected from the list consisting of an infant, a young child, a child, a teenager or an adult. It is particularly preferred that the individual is an infant or a young child.

In a further particular embodiment of the first aspect, the individual is a formula-fed infant.

In another particular embodiment of the first aspect, the individual is preterm, small for gestational age (SGA) and/or with a low birth weight (LBW), and preferably the individual is a preterm infant, a small for gestational age (SGA) infant and/or a low birth weight (LBW) infant.

In a specific embodiment of the first aspect, the nutritional composition is administered to the individual as the only feeding source or in addition to breast feeding.

In another preferred embodiment of the nutritional composition according to the first aspect, said composition is an infant formula, such as a starter infant formula, a follow-on formula (or follow-up formula) or a preterm infant formula, a milk fortifier, preferably a human milk fortifier, a growing-up milk, a baby food formula, a medical food product for clinical nutrition, a complement, a supplement, yogurt, juice, or a cereal bar. Even more preferably, said composition is an infant formula, a human milk fortifier, or a supplement.

A further particular embodiment relates to the nutritional composition according to the first aspect for use in enhancing learning skills and/or enhancing memory function in an individual, by enhancing neuroplasticity in the brain of an individual.

A further embodiment relates to the nutritional composition according to the first aspect for use in enhancing learning skills and/or enhancing memory function in an individual, by enhancing neurodevelopment, myelination, neurogenesis, axonal sprouting and/or maturation in the brain of an individual.

A further particular embodiment relates to the nutritional composition according to the first aspect for use in enhancing functions of perception, motor control, self-awareness, cognitive functioning and/or interpersonal experience in an individual.

In a second aspect, the invention relates to the use of a nutritional composition comprising 3'-Siallylactose (3'-SL) and 6'-Siallylactose (6'-SL) for enhancing learning skills and/or memory function in an individual, wherein 3'-Siallylactose (3'-SL) and 6'-Siallylactose (6'-SL) are comprised in the nutritional composition in a weight ratio between 10:1 and 1:10.

In a preferred embodiment of this nutritional composition, 3'-Siallylactose (3'-SL) and 6'-Siallylactose (6'-SL) are comprised in a weight ratio between 10:1 and 2:1, preferably between 8:1 and 3:1, between 6:1 and 3:1, between 5:1 and 3:1, between 5:1 and 4:1, or between 4.7:1 and 4.1:1, and most preferably in a ratio of 4.4:1.

In another preferred embodiment of this nutritional composition, 3'-Siallylactose (3'-SL) and 6'-Siallylactose (6'-SL) are comprised in a weight ratio between 6:1 and 1:10, preferably between 5.9:1 and 1.5:10, more preferably between 5.86:1 and 1.53:10, and most preferably in a ratio of 1:1.

In a particular embodiment of the second aspect, 3'-Siallylactose (3'-SL) and 6'-Siallylactose (6'-SL) are comprised in the nutritional composition in an amount of from 50 mg to 2500 mg of total sialyllactose per L of the nutritional composition, preferably from 60 mg to 2000 mg of total sialyllactose per L of the nutritional composition, more preferably from 80 mg to 1000 mg of total sialyllactose per L of the nutritional composition and most preferably from 87.5 mg to 735 mg of total sialyllactose per L of the nutritional composition.

In a specific embodiment of the second aspect, the nutritional composition is administered to the individual during the early age of said individual, and preferably during the infant phase of said individual.

It is further preferred that the nutritional composition is administered to the individual during the first 12 months after birth, during the first 8 months after birth, or during the first 6 months after birth, and more preferably during the first 4 months after birth, or during the first 2 months after birth.

In another particular embodiment of the second aspect, 3'-Siallylactose (3'-SL) and 6'-Siallylactose (6'-SL) are administered to the individual in an amount effective to provide from 110 mg to 180 mg, preferably from 120 mg to 170 mg, more preferably from 125 mg to 165 mg of total sialyllactose per kg body weight per day, and most preferably in an amount effective to provide 131 mg or 162 mg of total sialyllactose per kg body weight per day. It is preferred that 3'-Siallylactose (3'-SL) and 6'-Siallylactose (6'-SL) are administered to the individual during the first two weeks after birth in an amount effective to provide from 140 mg to 180 mg, preferably from 150 mg to 170 mg, more preferably from 160 mg to 165 mg and most preferably 162 mg of total sialyllactose per/kg body weight per day, It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide and from 110 mg to 150 mg, preferably from 120 mg to 140 mg, more preferably from 125 mg to 135 mg and most preferably 131 mg of total sialyllactose per/kg body weight per day.

In yet another particular embodiment of the nutritional composition of the second aspect, 3'-Siallylactose (3'-SL) and 6'-Siallylactose (6'-SL) are administered to the individual in an amount corresponding to from 350 mg to 530 mg, preferably from 380 mg to 500 mg, more preferably from 390 mg to 490 mg of N-Acetyl-neuraminic acid (Neu5Ac) per kg body weight per day, and most preferably in an amount corresponding to 393 mg or 487 mg of N-Acetyl-neuraminic acid (Neu5Ac) per kg body weight per day. It is preferred that 3'-Siallylactose (3'-SL) and 6'-Siallylactose (6'-SL) are administered to the individual during the first two weeks after birth in an amount corresponding to from 450 mg to 530 mg, preferably to from 480 mg to 500 mg, more preferably to from 485 mg to 490 mg and most preferably to 487 mg of N-Acetyl-neuraminic acid (Neu5Ac) per kg body weight per day. It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide from 350 mg to 430 mg, preferably from 380 mg to 400 mg, more preferably from 390 mg to 395 mg and most preferably 393 mg of N-Acetyl-neuraminic acid (Neu5Ac) per kg body weight per day.

In a preferred embodiment of the second aspect, learning skills and/or memory function in an individual are enhanced by increasing the sialic acid (Neu5Ac) concentration in the brain of said individual. Preferably, the sialic acid (Neu5Ac) concentration is increased in a brain region selected from hippocampus, frontal cortex, or a combination thereof. In a particularly preferred embodiment, learning skills and/or memory function in an individual are enhanced by increasing the sialic acid (Neu5Ac) concentration in the hippocampus of said individual.

In a further preferred embodiment of the second aspect, the use for enhancing memory function of an individual comprises enhancing long-term memory function.

In a further preferred embodiment of the second aspect, the use for enhancing memory function of an individual comprises enhancing short-term memory function.

In a further preferred embodiment of the second aspect, the use for enhancing memory function of an individual comprises enhancing both, short-term memory function and long-term memory function.

In a particular embodiment, the use according to the second aspect further comprises administering the nutritional composition to the individual as the only feeding source or in addition to breast feeding.

In another particular embodiment of the second aspect, learning skills and/or memory function in an individual are enhanced by enhancing neuroplasticity in the brain of said individual and/or by enhancing neurodevelopment, myelination, neurogenesis, axonal sprouting and/or maturation in the brain of said individual.

In a third aspect, the invention relates to the use of a nutritional composition comprising 3'-Siallylactose (3'-SL) and 6'-Siallylactose (6'-SL) for enhancing functions of perception, motor control, self-awareness, cognitive functioning and/or interpersonal experience in an individual, wherein, preferably, 3'-Siallylactose (3'-SL) and 6'-Siallylactose (6'-SL) are comprised in the nutritional composition in a weight ratio between 10:1 and 1:10.

In a preferred embodiment of this nutritional composition, 3'-Siallylactose (3'-SL) and 6'-Siallylactose (6'-SL) are comprised in a weight ratio between 10:1 and 2:1, preferably between 8:1 and 3:1, between 6:1 and 3:1, between 5:1 and 3:1, between 5:1 and 4:1, or between 4.7:1 and 4.1:1, and most preferably in a ratio of 4.4:1.

In another preferred embodiment of this nutritional composition, 3'-Siallylactose (3'-SL) and 6'-Siallylactose (6'-SL) are comprised in a weight ratio between 6:1 and 1:10, preferably between 5.9:1 and 1.5:10, more preferably between 5.86:1 and 1.53:10, and most preferably in a ratio of 1:1.

In a particular embodiment of the third aspect, 3'-Sialyllactose (3'-SL) and 6'-Sialyllactose (6'-SL) are comprised in the nutritional composition in an amount of from 50 mg to 2500 mg of total sialyllactose per L of the nutritional composition, preferably from 60 mg to 2000 mg of total sialyllactose per L of the nutritional composition, more preferably from 80 mg to 1000 mg of total sialyllactose per L of the nutritional composition and most preferably from 87.5 mg to 735 mg of total sialyllactose per L of the nutritional composition.

In a specific embodiment of the third aspect, the nutritional composition is administered to the individual during the early age of said individual, and preferably during the infant phase of said individual.

It is further preferred that the nutritional composition is administered to the individual during the first 12 months after birth, during the first 8 months after birth, or during the first 6 months after birth, and more preferably during the first 4 months after birth, or during the first 2 months after birth.

In another particular embodiment of the third aspect, 3'-Siallylactose (3'-SL) and 6'-Siallylactose (6'-SL) are administered to the individual in an amount effective to provide from 110 mg to 180 mg, preferably from 120 mg to 170 mg, more preferably from 125 mg to 165 mg of total sialyllactose per kg body weight per day, and most preferably in an amount effective to provide 131 mg or 162 mg of total sialyllactose per kg body weight per day. It is preferred that 3'-Siallylactose (3'-SL) and 6'-Siallylactose (6'-SL) are administered to the individual during the first two weeks after birth in an amount effective to provide from 140 mg to 180 mg, preferably from 150 mg to 170 mg, more preferably from 160 mg to 165 mg and most preferably 162 mg of total sialyllactose per/kg body weight per day, It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide and from 110 mg to 150 mg, preferably from 120 mg to 140 mg, more preferably from 125 mg to 135 mg and most preferably 131 mg of total sialyllactose per kg body weight per day.

In yet another particular embodiment of the use according to the third aspect, 3'-Siallylactose (3'-SL) and 6'-Siallylactose (6'-SL) are administered to the individual in an amount corresponding to from 350 mg to 530 mg, preferably from 380 mg to 500 mg, more preferably from 390 mg to 490 mg of N-Acetyl-neuraminic acid (Neu5Ac) per kg body weight per day, and most preferably in an amount corresponding to 393 mg or 487 mg of N-Acetyl-neuraminic acid (Neu5Ac) per kg body weight per day. It is preferred that 3'-Siallylactose (3'-SL) and 6'-Siallylactose (6'-SL) are administered to the individual during the first two weeks after birth in an amount corresponding to from 450 mg to 530 mg, preferably to from 480 mg to 500 mg, more preferably to from 485 mg to 490 mg and most preferably to 487 mg of N-Acetyl-neuraminic acid (Neu5Ac) per kg body weight per day. It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide from 350 mg to 430 mg, preferably from 380 mg to 400 mg, more preferably from 390 mg to 395 mg and most preferably 393 mg of N-Acetyl-neuraminic acid (Neu5Ac) per kg body weight per day.

In a preferred embodiment of the use according to the third aspect, functions of perception, motor control, self-awareness, cognitive functioning and/or interpersonal experience in an individual are enhanced by increasing the grey matter volume in the region of Insular cortex, Somatosensory cortex, Parahippocampal, Superior temporal and/or Cerebellar lobule in the brain of said individual.

In another preferred embodiment, the use according to the third aspect further comprises administering the nutritional composition to the individual as the only feeding source or in addition to breast feeding.

In a fourth aspect, the invention relates to the use of a nutritional composition comprising 3'-Siallylactose (3'-SL) and 6'-Siallylactose (6'-SL) for increasing the sialic acid (Neu5Ac) concentration in the brain of an individual, preferably wherein the sialic acid (Neu5Ac) concentration is increased in a brain region selected from hippocampus, frontal cortex, or a combination thereof. In a particularly preferred embodiment, the sialic acid (Neu5Ac) concentration is increased in the hippocampus of the individual.

In a preferred embodiment of this aspect, 3'-Siallylactose (3'-SL) and 6'-Siallylactose (6'-SL) are comprised in the nutritional composition in a weight ratio between 10:1 and 1:10.

In a particularly preferred embodiment of this nutritional composition, 3'-Siallylactose (3'-SL) and 6'-Siallylactose (6'-SL) are comprised in a weight ratio between 10:1 and 2:1, preferably between 8:1 and 3:1, between 6:1 and 3:1, between 5:1 and 3:1, between 5:1 and 4:1, or between 4.7:1 and 4.1:1, and most preferably in a ratio of 4.4:1.

In another preferred embodiment of this nutritional composition, 3'-Siallylactose (3'-SL) and 6'-Siallylactose (6'-SL) are comprised in a weight ratio between 6:1 and 1:10, preferably between 5.9:1 and 1.5:10, more preferably between 5.86:1 and 1.53:10, and most preferably in a ratio of 1:1.

In a particular embodiment of the fourth aspect, 3'-Sialyllactose (3'-SL) and 6'-Sialyllactose (6'-SL) are comprised in the nutritional composition in an amount of from 50 mg to 2500 mg of total sialyllactose per L of the nutritional composition, preferably from 60 mg to 2000 mg of total sialyllactose per L of the nutritional composition, more preferably from 80 mg to 1000 mg of total sialyllactose per L of the nutritional composition and most preferably from 87.5 mg to 735 mg of total sialyllactose per L of the nutritional composition.

In a specific embodiment of the fourth aspect, the nutritional composition is administered to the individual during the early age of said individual, and preferably during the infant phase of said individual.

It is further preferred that the nutritional composition is administered to the individual during the first 12 months after birth, during the first 8 months after birth, or during the first 6 months after birth, and more preferably during the first 4 months after birth, or during the first 2 months after birth.

In another particular embodiment of the fourth aspect, 3'-Siallylactose (3'-SL) and 6'-Siallylactose (6'-SL) are administered to the individual in an amount effective to provide from 110 mg to 180 mg, preferably from 120 mg to 170 mg, more preferably from 125 mg to 165 mg of total sialyllactose per kg body weight per day, and most preferably in an amount effective to provide 131 mg or 162 mg of total sialyllactose per kg body weight per day. It is preferred that 3'-Siallylactose (3'-SL) and 6'-Siallylactose (6'-SL) are administered to the individual during the first two weeks after birth in an amount effective to provide from 140 mg to 180 mg, preferably from 150 mg to 170 mg, more preferably from 160 mg to 165 mg and most preferably 162 mg of total sialyllactose per/kg body weight per day, It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide and from 110 mg to 150 mg, preferably from 120 mg to 140 mg, more preferably from 125 mg to 135 mg and most preferably 131 mg of total sialyllactose per kg body weight per day.

In yet another particular embodiment of the use according to the fourth aspect, 3'-Siallylactose (3'-SL) and 6'-Siallylactose (6'-SL) are administered to the individual in an amount corresponding to from 350 mg to 530 mg, preferably from 380 mg to 500 mg, more preferably from 390 mg to 490 mg of N-Acetyl-neuraminic acid (Neu5Ac) per kg body weight per day, and most preferably in an amount corresponding to 393 mg or 487 mg of N-Acetyl-neuraminic acid (Neu5Ac) per kg body weight per day. It is preferred that 3'-Siallylactose (3'-SL) and 6'-Siallylactose (6'-SL) are administered to the individual during the first two weeks after birth in an amount corresponding to from 450 mg to 530 mg, preferably to from 480 mg to 500 mg, more preferably to from 485 mg to 490 mg and most preferably to 487 mg of N-Acetyl-neuraminic acid (Neu5Ac) per kg body weight per day. It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide from 350 mg to 430 mg, preferably from 380 mg to 400 mg, more preferably from 390 mg to 395 mg and most preferably 393 mg of N-Acetyl-neuraminic acid (Neu5Ac) per kg body weight per day.

In a further preferred embodiment of the fourth aspect, increasing the sialic acid (Neu5Ac) concentration in the brain of an individual enhances memory function of an individual, preferably long-term memory function and/or short-term memory function.

In another preferred embodiment, the use according to the fourth aspect further comprises administering the nutritional composition to the individual as the only feeding source or in addition to breast feeding.

In a fifth aspect, the invention relates to a method for enhancing learning skills and/or enhancing memory function in an individual, especially by increasing the sialic acid (Neu5Ac) concentration in the brain of said individual, said method comprising administering to said individual a nutritional composition comprising 3'-Siallylactose (3'-SL) and 6'-Siallylactose (6'-SL) in a weight ratio between 10:1 and 1:10.

In a preferred embodiment of this method, 3'-Siallylactose (3'-SL) and 6'-Siallylactose (6'-SL) are comprised in the nutritional composition in a weight ratio between 10:1 and 2:1, preferably between 8:1 and 3:1, between 6:1 and 3:1, between 5:1 and 3:1, between 5:1 and 4:1, or between 4.7:1 and 4.1:1, and most preferably in a ratio of 4.4:1.

In another preferred embodiment of this method, 3'-Siallylactose (3'-SL) and 6'-Siallylactose (6'-SL) are comprised in the nutritional composition in a weight ratio between 6:1 and 1:10, preferably between 5.9:1 and 1.5:10, more preferably between 5.86:1 and 1.53:10, and most preferably in a ratio of 1:1.

In a particular embodiment of the fifth aspect, 3'-Siallylactose (3'-SL) and 6'-Siallylactose (6'-SL) are comprised in the nutritional composition in an amount of from 50 mg to 2500 mg of total sialyllactose per L of the nutritional composition, preferably from 60 mg to 2000 mg of total sialyllactose per L of the nutritional composition, more preferably from 80 mg to 1000 mg of total sialyllactose per L of the nutritional composition and most preferably from 87.5 mg to 735 mg of total sialyllactose per L of the nutritional composition.

In a specific embodiment of the fifth aspect, the nutritional composition is administered to the individual during the early age of said individual, and preferably during the infant phase of said individual.

It is further preferred that the nutritional composition is administered to the individual during the first 12 months after birth, during the first 8 months after birth, or during the first 6 months after birth, and more preferably during the first 4 months after birth, or during the first 2 months after birth.

In another particular embodiment of the method according to the fifth aspect, 3'-Siallylactose (3'-SL) and 6'-Siallylactose (6'-SL) are administered to the individual in an amount effective to provide from 110 mg to 180 mg, preferably from 120 mg to 170 mg, more preferably from 125 mg to 165 mg of total sialyllactose per kg body weight per day, and most preferably in an amount effective to provide 131 mg or 162 mg of total sialyllactose per kg body weight per day. It is preferred that 3'-Siallylactose (3'-SL) and 6'-Siallylactose (6'-SL) are administered to the individual during the first two weeks after birth in an amount effective to provide from 140 mg to 180 mg, preferably from 150 mg to 170 mg, more preferably from 160 mg to 165 mg and most preferably 162 mg of total sialyllactose per kg body weight per day, It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide and from 110 mg to 150 mg, preferably from 120 mg to 140 mg, more preferably from 125 mg to 135 mg and most preferably 131 mg of total sialyllactose per kg body weight per day.

In yet another particular embodiment of the method according to the fifth aspect, 3'-Siallylactose (3'-SL) and 6'-Siallylactose (6'-SL) are administered to the individual in an amount corresponding to from 350 mg to 530 mg, preferably from 380 mg to 500 mg, more preferably from 390 mg to 490 mg of N-Acetyl-neuraminic acid (Neu5Ac) per kg body weight per day, and most preferably in an amount corresponding to 393 mg or 487 mg of N-Acetyl-neuraminic acid (Neu5Ac) per kg body weight per day. It is preferred that 3'-Siallylactose (3'-SL) and 6'-Siallylactose (6'-SL) are administered to the individual during the first two weeks after birth in an amount corresponding to from 450 mg to 530 mg, preferably to from 480 mg to 500 mg, more preferably to from 485 mg to 490 mg and most preferably to 487 mg of N-Acetyl-neuraminic acid (Neu5Ac) per kg body weight per day. It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide from 350 mg to 430 mg, preferably from 380 mg to 400 mg, more preferably from 390 mg to 395 mg and most preferably 393 mg of N-Acetyl-neuraminic acid (Neu5Ac) per kg body weight per day.

In a preferred embodiment of the fifth aspect, learning skills and/or memory function in an individual are enhanced by increasing the sialic acid (Neu5Ac) concentration in a brain region selected from hippocampus, frontal cortex, or a combination thereof. In a particularly preferred embodiment, learning skills and/or memory function in an individual are enhanced by increasing the sialic acid (Neu5Ac) concentration in the hippocampus of said individual.

In a further preferred embodiment of the fifth aspect, the method for enhancing memory function of an individual comprises enhancing long-term memory function.

In a further preferred embodiment of the fifth aspect, the method for enhancing memory function of an individual comprises enhancing short-term memory function.

In a further preferred embodiment of the fifth aspect, the method for enhancing memory function of an individual comprises enhancing both, short-term memory function and long-term memory function.

In another preferred embodiment of the method according to the fifth aspect, the nutritional composition is administered to the individual as the only feeding source or in addition to breast feeding.

In a sixth aspect, the invention relates to a method for enhancing learning skills and/or enhancing memory function in an individual, by enhancing neuroplasticity in the brain of said individual, and/or by enhancing neurodevelopment, myelination, neurogenesis, axonal sprouting and/or maturation in the brain of said individual, said method comprising administering to said individual a nutritional composition comprising 3'-Siallylactose (3'-SL) and 6'-Siallylactose (6'-SL) in a weight ratio between 10:1 and 1:10.

In a preferred embodiment of this method, 3'-Siallylactose (3'-SL) and 6'-Siallylactose (6'-SL) are comprised in the nutritional composition in a weight ratio between 10:1 and 2:1, preferably between 8:1 and 3:1, between 6:1 and 3:1, between 5:1 and 3:1, between 5:1 and 4:1, or between 4.7:1 and 4.1:1, and most preferably in a ratio of 4.4:1.

In another preferred embodiment of this method, 3'-Siallylactose (3'-SL) and 6'-Siallylactose (6'-SL) are comprised in the nutritional composition in a weight ratio between 6:1 and 1:10, preferably between 5.9:1 and 1.5:10, more preferably between 5.86:1 and 1.53:10, and most preferably in a ratio of 1:1.

In a particular embodiment of the sixth aspect, 3'-Siallylactose (3'-SL) and 6'-Siallyllactose (6'-SL) are comprised in the nutritional composition in an amount of from 50 mg to 2500 mg of total sialyllactose per L of the nutritional composition, preferably from 60 mg to 2000 mg of total sialyllactose per L of the nutritional composition, more preferably from 80 mg to 1000 mg of total sialyllactose per L of the nutritional composition and most preferably from 87.5 mg to 735 mg of total sialyllactose per L of the nutritional composition.

In a specific embodiment of the sixth aspect, the nutritional composition is administered to the individual during the early age of said individual, and preferably during the infant phase of said individual.

It is further preferred that the nutritional composition is administered to the individual during the first 12 months after birth, during the first 8 months after birth, or during the first 6 months after birth, and more preferably during the first 4 months after birth, or during the first 2 months after birth.

In another particular embodiment of the method according to the sixth aspect, 3'-Siallylactose (3'-SL) and 6'-Siallylactose (6'-SL) are administered to the individual in an amount effective to provide from 110 mg to 180 mg, preferably from 120 mg to 170 mg, more preferably from 125 mg to 165 mg of total sialyllactose per kg body weight per day, and most preferably in an amount effective to provide 131 mg or 162 mg of total sialyllactose per kg body weight per day. It is preferred that 3'-Siallylactose (3'-SL) and 6'-Siallylactose (6'-SL) are administered to the individual during the first two weeks after birth in an amount effective to provide from 140 mg to 180 mg, preferably from 150 mg to 170 mg, more preferably from 160 mg to 165 mg and most preferably 162 mg of total sialyllactose per kg body weight per day, It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide and from 110 mg to 150 mg, preferably from 120 mg to 140 mg, more preferably from 125 mg to 135 mg and most preferably 131 mg of total sialyllactose per kg body weight per day.

In yet another particular embodiment of the method according to the sixth aspect, 3'-Siallylactose (3'-SL) and 6'-Siallylactose (6'-SL) are administered to the individual in an amount corresponding to from 350 mg to 530 mg, preferably from 380 mg to 500 mg, more preferably from 390 mg to 490 mg of N-Acetyl-neuraminic acid (Neu5Ac) per kg body weight per day, and most preferably in an amount corresponding to 393 mg or 487 mg of N-Acetyl-neuraminic acid (Neu5Ac) per kg body weight per day. It is preferred that 3'-Siallylactose (3'-SL) and 6'-Siallylactose (6'-SL) are administered to the individual during the first two weeks after birth in an amount corresponding to from 450 mg to 530 mg, preferably to from 480 mg to 500 mg, more preferably to from 485 mg to 490 mg and most preferably to 487 mg of N-Acetyl-neuraminic acid (Neu5Ac) per kg body weight per day. It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide from 350 mg to 430 mg, preferably from 380 mg to 400 mg, more preferably from 390 mg to 395 mg and most preferably 393 mg of N-Acetyl-neuraminic acid (Neu5Ac) per kg body weight per day.

In a preferred embodiment of the sixth aspect, learning skills and/or memory function in an individual are enhanced by enhancing neuroplasticity in the brain of said individual, preferably in a brain region selected from hippocampus, frontal cortex, or a combination thereof. In a particularly preferred embodiment, learning skills and/or memory function in an individual are enhanced by enhancing neuroplasticity in the hippocampus of said individual.

In a further preferred embodiment of the sixth aspect, the method for enhancing memory function of an individual comprises enhancing long-term memory function.

In a further preferred embodiment of the sixth aspect, the method for enhancing memory function of an individual comprises enhancing short-term memory function.

In a further preferred embodiment of the sixth aspect, the method for enhancing memory function of an individual comprises enhancing both, short-term memory function and long-term memory function.

In another preferred embodiment of the method according to the sixth aspect, the nutritional composition is administered to the individual as the only feeding source or in addition to breast feeding.

In a seventh aspect, the invention relates to a method for enhancing functions of perception, motor control, self-awareness, cognitive functioning and/or interpersonal experience in an individual, said method comprising administering to said individual a nutritional composition comprising 3'-Siallylactose (3'-SL) and 6'-Siallylactose (6'-SL) in a weight ratio between 10:1 and 1:10.

In a preferred embodiment of this method, 3'-Siallylactose (3'-SL) and 6'-Siallylactose (6'-SL) are comprised in the nutritional composition in a weight ratio between 10:1 and 2:1, preferably between 8:1 and 3:1, between 6:1 and 3:1, between 5:1 and 3:1, between 5:1 and 4:1, or between 4.7:1 and 4.1:1, and most preferably in a ratio of 4.4:1.

In another preferred embodiment of this method, 3'-Siallylactose (3'-SL) and 6'-Siallylactose (6'-SL) are comprised in the nutritional composition in a weight ratio between 6:1 and 1:10, preferably between 5.9:1 and 1.5:10, more preferably between 5.86:1 and 1.53:10, and most preferably in a ratio of 1:1.

In a particular embodiment of the seventh aspect, 3'-Siallyllactose (3'-SL) and 6'-Siallylactose (6'-SL) are comprised in the nutritional composition in an amount of from 50 mg to 2500 mg of total sialyllactose per L of the nutritional composition, preferably from 60 mg to 2000 mg of total sialyllactose per L of the nutritional composition, more preferably from 80 mg to 1000 mg of total sialyllactose per L of the nutritional composition and most preferably from 87.5 mg to 735 mg of total sialyllactose per L of the nutritional composition.

In a specific embodiment of the seventh aspect, the nutritional composition is administered to the individual during the early age of said individual, and preferably during the infant phase of said individual.

It is further preferred that the nutritional composition is administered to the individual during the first 12 months after birth, during the first 8 months after birth, or during the first 6 months after birth, and more preferably during the first 4 months after birth, or during the first 2 months after birth.

In another particular embodiment of the method according to the seventh aspect, 3'-Siallylactose (3'-SL) and 6'-Siallylactose (6'-SL) are administered to the individual in an amount effective to provide from 110 mg to 180 mg, preferably from 120 mg to 170 mg, more preferably from 125 mg to 165 mg of total sialyllactose per kg body weight per day, and most preferably in an amount effective to provide 131 mg or 162 mg of total sialyllactose per kg body weight per day. It is preferred that 3'-Siallylactose (3'-SL) and 6'-Siallylactose (6'-SL) are administered to the individual during the first two weeks after birth in an amount effective to provide from 140 mg to 180 mg, preferably from 150 mg to 170 mg, more preferably from 160 mg to 165 mg and most preferably 162 mg of total sialyllactose per kg body weight per day, It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide and from 110 mg to 150 mg, preferably from 120 mg to 140 mg, more preferably from 125 mg to 135 mg and most preferably 131 mg of total sialyllactose per kg body weight per day.

In yet another particular embodiment of the method according to the seventh aspect, 3'-Siallylactose (3'-SL) and 6'-Siallylactose (6'-SL) are administered to the individual in an amount corresponding to from 350 mg to 530 mg, preferably from 380 mg to 500 mg, more preferably from 390 mg to 490 mg of N-Acetyl-neuraminic acid (Neu5Ac) per kg body weight per day, and most preferably in an amount corresponding to 393 mg or 487 mg of N-Acetyl-neuraminic acid (Neu5Ac) per kg body weight per day. It is preferred that 3'-Siallylactose (3'-SL) and 6'-Siallylactose (6'-SL) are administered to the individual during the first two weeks after birth in an amount corresponding to from 450 mg to 530 mg, preferably to from 480 mg to 500 mg, more preferably to from 485 mg to 490 mg and most preferably to 487 mg of N-Acetyl-neuraminic acid (Neu5Ac) per kg body weight per day. It is further preferred that 3'-Siallylactose (3'-SL) and 6'-Siallylactose (6'-SL) are administered to the individual from two weeks after birth and up to 12 months after birth, up to 8 months after birth, or up to 6 months after birth, and preferably from two weeks after birth and up to 4 months after birth, or up to 2 months after birth, in an amount effective to provide from 350 mg to 430 mg, preferably from 380 mg to 400 mg, more preferably from 390 mg to 395 mg and most preferably 393 mg of N-Acetyl-neuraminic acid (Neu5Ac) per kg body weight per day.

In a preferred embodiment of the seventh aspect, functions of perception, motor control, self-awareness, cognitive functioning and/or interpersonal experience in an individual are enhanced by increasing the grey matter volume in the region of Insular cortex, Somatosensory cortex, Parahippocampal, Superior temporal and/or Cerebellar lobule in the brain of said individual.

In another preferred embodiment of the method according to the seventh aspect, the nutritional composition is administered to the individual as the only feeding source or in addition to breast feeding.

In a preferred embodiment of any of the above uses or methods (i.e. of any one of the second, third, fourth, fifth, sixth and seventh aspects of the invention), 3'-Siallylactose (3'-SL) and 6'-Siallylactose (6'-SL) are comprised in a nutritional composition in a weight ratio between 10:1 and 2:1, preferably between 8:1 and 3:1, between 6:1 and 3:1, between 5:1 and 3:1, between 5:1 and 4:1, or between 4.7:1 and 4.1:1, and most preferably in a ratio of 4.4:1.

In another preferred embodiment of any of the above uses or methods, 3'-Siallylactose (3'-SL) and 6'-Siallylactose (6'-SL) are comprised in a nutritional composition in a weight ratio between 6:1 and 1:10, preferably between 5.9:1 and 1.5:10, more preferably between 5.86:1 and 1.53:10, and most preferably in a ratio of 1:1.

In a particular embodiment of any of the above uses or methods, 3'-Siallylactose (3'-SL) and 6'-Siallylactose (6'-SL) are comprised in a nutritional composition in an amount of from 50 mg to 2500 mg of total sialyllactose per L of the nutritional composition, preferably from 60 mg to 2000 mg of total sialyllactose per L of the nutritional composition, more preferably from 80 mg to 1000 mg of total sialyllactose per L of the nutritional composition and most preferably from 87.5 mg to 735 mg of total sialyllactose per L of the nutritional composition.

In a specific embodiment of any of the above uses or methods, a nutritional composition is administered to an individual during the early age of said individual, and preferably during the infant phase of said individual.

It is further preferred that in any of the above uses or methods a nutritional composition is administered to an individual during the first 12 months after birth, during the first 8 months after birth, or during the first 6 months after birth, and more preferably during the first 4 months after birth, or during the first 2 months after birth.

In another particular embodiment of any of the above uses or methods, 3'-Siallylactose (3'-SL) and 6'-Siallylactose (6'-SL) are administered to an individual in an amount effective to provide from 110 mg to 180 mg, preferably from 120 mg to 170 mg, more preferably from 125 mg to 165 mg of total sialyllactose per kg body weight per day, and most preferably in an amount effective to provide 131 mg or 162 mg of total sialyllactose per kg body weight per day.

It is preferred that in any of the above uses or methods 3'-Siallylactose (3'-SL) and 6'-Siallylactose (6'-SL) are administered to an individual during the first two weeks after birth in an amount effective to provide from 140 mg to 180 mg, preferably from 150 mg to 170 mg, more preferably from 160 mg to 165 mg and most preferably 162 mg of total sialyllactose per kg body weight per day, It is further preferred that in any of the above uses or methods 3'-Siallylactose (3'-SL) and 6'-Siallylactose (6'-SL) are administered to an individual from two weeks after birth and up to 12 months after birth, up to 8 months after birth, or up to 6 months after birth, and preferably from two weeks after birth and up to 4 months after birth, or up to 2 months after birth, in an amount effective to provide and from 110 mg to 150 mg, preferably from 120 mg to 140 mg, more preferably from 125 mg to 135 mg and most preferably 131 mg of total sialyllactose per kg body weight per day.

In yet another particular embodiment of any of the above uses or methods, 3'-Siallylactose (3'-SL) and 6'-Siallylactose (6'-SL) are administered to an individual in an amount corresponding to from 350 mg to 530 mg, preferably from 380 mg to 500 mg, more preferably from 390 mg to 490 mg of N-Acetyl-neuraminic acid (Neu5Ac) per kg body weight per day, and most preferably in an amount corresponding to 393 mg or 487 mg of N-Acetyl-neuraminic acid (Neu5Ac) per kg body weight per day.

It is preferred that in any of the above uses or methods 3'-Siallylactose (3'-SL) and 6'-Siallylactose (6'-SL) are administered to an individual during the first two weeks after birth in an amount corresponding to from 450 mg to 530 mg, preferably to from 480 mg to 500 mg, more preferably to from 485 mg to 490 mg and most preferably to 487 mg of N-Acetyl-neuraminic acid (Neu5Ac) per kg body weight per day.

It is further preferred that in any of the above uses or methods 3'-Siallylactose (3'-SL) and 6'-Siallylactose (6'-SL) are administered to an individual from two weeks after birth and up to 12 months after birth, up to 8 months after birth, or up to 6 months after birth, and preferably from two weeks after birth and up to 4 months after birth, or up to 2 months after birth, in an amount effective to provide from 350 mg to 430 mg, preferably from 380 mg to 400 mg, more preferably from 390 mg to 395 mg and most preferably 393 mg of N-Acetyl-neuraminic acid (Neu5Ac) per kg body weight per day. In another preferred embodiment of any of the above uses or methods (i.e. from the second to the seventh aspects of the invention), the individual is a mammal, more preferably a pet or a human, and most preferably a human.

In yet another preferred embodiment of any of these uses or methods, the individual is selected from an infant, a young child, a child, a teenager or an adult. It is particularly preferred that the individual is an infant or a young child.

In a further particular embodiment of any of the above uses or methods, the individual is a formula-fed infant.

In a yet further preferred embodiment of any of the above uses or methods, the individual is preterm, small for gestational age (SGA) and/or with a low birth weight (LBW), and preferably the individual is a preterm infant, a small for gestational age (SGA) infant and/or a low birth weight (LBW) infant.

In a further preferred embodiment of any of the above uses or methods, the nutritional composition is an infant formula, such as a starter infant formula, a follow-on formula (or follow-up formula) or a preterm infant formula, a milk fortifier, preferably a human milk fortifier, a growing-up milk, a baby food formula, a medical food product for clinical nutrition, a complement, a supplement, yogurt, juice, or a cereal bar. Even more preferably, said composition is an infant formula, a human milk fortifier, or a supplement.

Other aspects and embodiments of the present invention are described below.

BRIEF DESCRIPTION OF THE FIGURES

FIG. 7A depicts N-Acetylneuraminic acid concentration in brain hippocampus. FIG. 7B depicts N-Glycolylneuraminic acid concentration in brain hippocampus. FIG. 7C depicts N-Acetylneuraminic acid concentration in brain frontal cortex. FIG. 7D depicts N-Glycolylneuraminic acid concentration in brain frontal cortex.

FIG. 8 displays a summary of the results obtained from Example 2 and 3.

DETAILED DESCRIPTION

Figure 1:
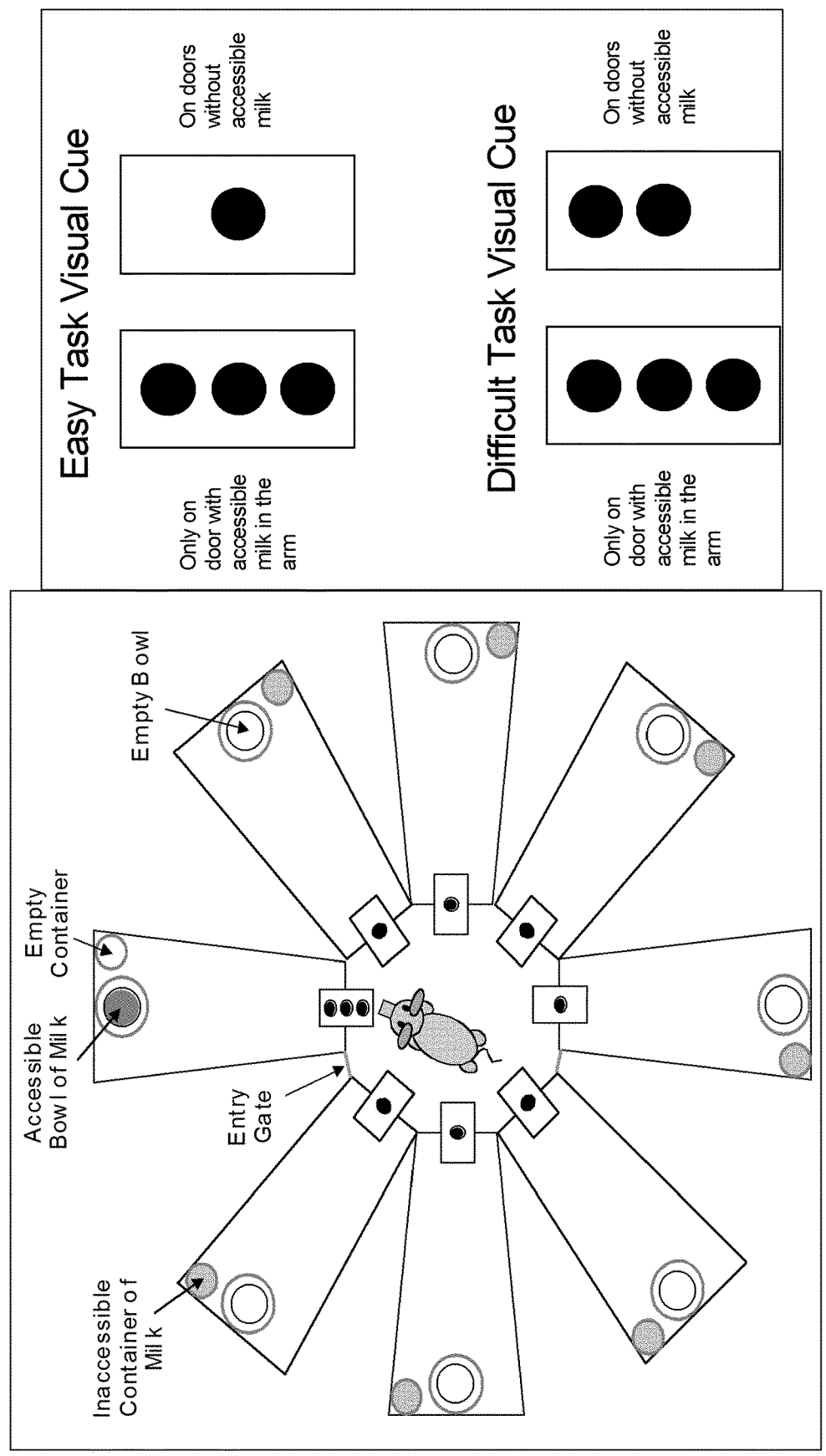
FIG. 1 depicts a schematic representation of the learning area with an 8-arm radial maze and the visual cues used for assessing learning and memory function according to Example 2.

The present inventors surprisingly found that nutritional supplementation with oligosaccharide-bound sialic acid in the form of siallyllactose could improve learning skills and memory functions in an individual by increasing the sialic acid (Neu5Ac) concentration in the brain of said individual, particularly in the hippocampus and/or the frontal cortex of said individual.

Individual

In the context of the invention, the term "individual" refers to a mammal such as a human or an animal, and, preferably, to a human or a pet. In a particularly preferred embodiment the individual is a human.

Further, said individual may be an infant preferably a human infant, a young child, a child, a teenager or an adult. Preferably, the individual is a human infant or a young child.

In the context of the present invention, the term "infant" or "infants" means children under the age of 12 months. Further, in the present context, the term "young child" or "young children" means children between one and three years of age.

In a particular embodiment, the individual is a formula-fed infant, i.e. an infant exclusively fed a formula, especially infant formula or a formula supplemented/fortified with a fortifier for example, more preferably infant exclusively fed infant formula.

Moreover, the individual may be preterm, small for gestational age (SGA) and/or with a low birth weight (LBW), and it may especially be a preterm infant, a small for gestational age (SGA) infant and/or a low birth weight (LBW) infant.

A "preterm" or "premature" means an infant or young child who was not born at term. Generally it refers to an infant or young child born prior 36 weeks of gestation.

By the expression "small for gestational age" or "SGA" it is referred to an infant or young child who is smaller in size than normal for their gestational age at birth, most commonly defined as a weight below the 10th percentile for the gestational age. In some embodiments, SGA may be associated with Intrauterine growth restriction (IUGR), which refers to a condition in which a foetus is unable to achieve its potential size.

The expression "low birth weight" is to be understood as any body weight under 2500 g at birth. It therefore encompasses:
  infant or young child who has/had a body weight from 1800 to 2500 g at birth (usually called "low birth weight" or LBW)
  infant or young child who has/had a body weight from 1000 to 1800 g at birth (called "very low birth weight" or VLBW)
  infant or young child who has/had a body weight under 1000 g at birth (called "extremely low birth weight" or ELBW)

Infants or young children with low birth weight may or may not be preterm, and similarly, infants or young children who were small for gestational age may or may not be preterm.

In an embodiment, the individual may also be an elderly human or an elderly animal, preferably an elderly pet. Within the present context, an elderly human is at least 60 years of age, and preferably at least 65 years of age. The onset age for an elderly animal or pet may vary depending on the species of the animal or pet. For instance, an elderly cat or dog may be at least 7 years of age, preferably at least 8 years of age, The individual may also be a pregnant human or a pregnant animal, preferably a pregnant pet.

Sialyllactose and Use Thereof

Sialyllactose (SL) belongs to the acidic human milk oligosaccharides. The trisaccharide sialyllactose consists of lactose at the reducing terminus and one sialic acid residue at the non-reducing end via an α-2,3 binding or α-2,6 binding, resulting in 3'-sialyllactose (3'-SL) and 6'-sialyllactose (6'-SL), respectively.

Accordingly, as used herein, the terms "sialyllactose", "sialyllactose (SL)" and "SL" are equal and refer to both, 3'-sialyllactose (3'-SL) and 6'-sialyllactose (6'-SL). Further, the terms "total sialyllactose", "total sialyllactose (SL)" and "total SL" are equal and refer to the total quantity of both, 3'-sialyllactose (3'-SL) and 6'-sialyllactose (6'-SL).

The inventors demonstrated for the first time that providing an individual with both, 3'-sialyllactose (3'-SL) and 6'-sialyllactose (6'-SL) significantly enhances learning skills and memory function in an individual. Accordingly, the present invention refers to the use of 3'-sialyllactose (3'-SL) and 6'-sialyllactose (6'-SL) for enhancing learning skills and/or memory function in an individual.

In the context of the present disclosure, "3'-sialyllactose" (3'-SL, 3-SL, 3'SL, or 3SL), refers to (6R)-5-Acetamido-3,5-dideoxy-6-[(1R,2R)-1,2,3-trihydroxypropyl]-β-L-threo-hex-2-ulopyranonosyl-(2->3)-β-D-galactopyranosyl-(1->4)-D-glucopyranose (IUPAC), and "6'-sialyllactose" (6'-SL, 6-SL, 6'SL, or 6SL) refers to (6R)-5-Acetamido-3,5-dideoxy-6-[(1R,2R)-1,2,3-trihydroxypropyl]-β-L-threo-hex-2-ulopyranonosyl-(2->6)-β-D-galactopyranosyl-(1->4)-D-glucopyranose (IUPAC).

The 3'- and 6'-forms of sialyllactose may be isolated by chromatographic or filtration technology from a natural source such as animal milks. Alternatively, they may be produced by biotechnological means using specific sialyl-transferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo, Japan, or from GeneChem, Republic of Korea.

As used herein, the expression "learning skills" is to be understood as referring to the information processing abilities of an individual, including perception, learning, remembering, judging and problem solving. "Learning skills" also include the ability of an individual to acquire new, or modify and reinforce, existing knowledge, behaviors, skills, values, or preferences and may involve generating different types of information.

In a preferred embodiment of the present invention, the expression "learning skills" encompasses the expression "learning speed". "Learning speed" is to be understood as referring to the time an individual needs for information processing, including perception, learning, remembering, judging and problem solving. "Learning speed" also includes the time an individual needs to acquire new, or modify and reinforce, existing knowledge, behaviors, skills, values, or preferences, or to generate different types of information.

In the present context, the expression "memory function" is to be understood as referring to short-term memory function or long-term memory function, or, preferably, to both, short-term memory function and long-term memory function.

It was further found that the enhanced learning skills and memory function in individuals after dietary sialyllactose supplementation as disclosed herein are particularly due to a significant increase in the sialic acid (Neu5Ac) concentration in the brains of these individuals. More specifically, dietary sialyllactose supplementation was found to increase the sialic acid (Neu5Ac) concentration in specific brain regions such as brain hippocampus and frontal cortex, and particularly in hippocampus. These findings further indicate that the present dietary sialyllactose supplementation also enhances neuroplasticity in the brain of an individual.

Thus, the present invention particularly relates to the use of 3'-sialyllactose (3'-SL) and 6'-sialyllactose (6'-SL) for enhancing learning skills and/or memory function in an individual by increasing the sialic acid (Neu5Ac) concentration in the brain of said individual and/or by enhancing neuroplasticity in the brain of said individual.

Moreover, the present inventors found that dietary sialyllactose supplementation according to the present disclosure significantly increases the grey matter volume in several regions of brain including the region of insular cortex, somatosensory cortex, parahippocampal, superior temporal and cerebellar lobule, thus enhancing functions of perception, motor control, self-awareness, cognitive functioning and/or interpersonal experience in an individual.

In accordance with these findings, the invention also relates to the use of 3'-sialyllactose (3'-SL) and 6'-sialyllactose (6'-SL) for enhancing functions of perception, motor control, self-awareness, cognitive functioning and/or interpersonal experience in an individual.

The above described effects may be achieved in an individual by administering to said individual any combination of 3'-sialyllactose (3'-SL) and 6'-sialyllactose (6'-SL). However, in the present context, 3'-SL and 6'-SL are preferably used or administered in a weight ratio of between 10:1 and 1:10, more preferably between 10:1 and 2:1, between 8:1 and 3:1, between 6:1 and 3:1, between 5:1 and 3:1, between 5:1 and 4:1, or between 4.7:1 and 4.1:1, such as in a ratio of 4.4:1.

In another particular embodiment, 3'-SL and 6'-SL are preferably used or administered in a weight ratio of between 6:1 and 1:10, between 5.9:1 and 1.5:10, or between 5.86:1 and 1.53:10, and most preferably in a ratio of 1:1. In this embodiment, the individual is preferably a human such as human infant or a young child.

Further, 3'-sialyllactose (3'-SL) and 6'-sialyllactose (6'-SL) are preferably used or administered to an individual during the early age of said individual, such as during the infant phase of said individual. In the present context, the term "infant phase" refers to the first year of an infant's life, i.e. to the first 12 months after birth of said infant.

More preferably, 3'-sialyllactose (3'-SL) and 6'-sialyllactose (6'-SL) are used or administered to an individual during the first 8 months after birth, or during the first 6 months after birth, and preferably during the first 4 months after birth, or during the first 2 months after birth.

Moreover, 3'-Siallylactose (3'-SL) and 6'-Siallylactose (6'-SL) are preferably used or administered to an individual in an amount effective to provide from 110 mg to 180 mg, from 120 mg to 170 mg, or from 125 mg to 165 mg of total sialyllactose per kg body weight per day, such as in an amount effective to provide 131 mg of total sialyllactose per kg body weight per day, or in an amount effective to provide 162 mg of total sialyllactose per kg body weight per day.

In a particular embodiment, 3'-Siallylactose (3'-SL) and 6'-Siallylactose (6'-SL) are administered to an individual during the first two weeks after birth in an amount effective to provide from 140 mg to 180 mg, from 150 mg to 170 mg, or from 160 mg to 165 mg of total sialyllactose per kg body weight per day, such as in an amount of 162 mg of total sialyllactose per kg body weight per day, From two weeks after birth and up to 12 months after birth, such as up to 8 months, up to 6 months or, preferably, up to 4 months after birth of said individual, 3'-Siallylactose (3'-SL) and 6'-Siallylactose (6'-SL) are preferably administered in an amount effective to provide and from 110 mg to 150 mg, from 120 mg to 140 mg, or from 125 mg to 135 mg of total sialyllactose per kg body weight per day, such as in an amount effective to provide 131 mg of total sialyllactose per kg body weight per day.

It is further preferred that 3'-Siallylactose (3'-SL) and 6'-Siallylactose (6'-SL) are administered to an individual in an amount corresponding to from 350 mg to 530 mg, from 380 mg to 500 mg, or from 390 mg to 490 mg of N-Acetyl-neuraminic acid (Neu5Ac) per kg body weight per day, such as in an amount corresponding to 393 mg of N-Acetyl-neuraminic acid (Neu5Ac) per kg body weight per day, or in an amount corresponding to 487 mg of N-Acetyl-neuraminic acid (Neu5Ac) per kg body weight per day.

In a particular embodiment, 3'-Siallylactose (3'-SL) and 6'-Siallylactose (6'-SL) are administered to an individual during the first two weeks after birth in an amount corresponding to from 450 mg to 530 mg, from 480 mg to 500 mg, or from 485 mg to 490 mg per kg body weight per day, such as in an amount corresponding to 487 mg of N-Acetyl-neuraminic acid (Neu5Ac) per kg body weight per day.

From two weeks after birth and up to 12 months after birth, such as up to 8 months, up to 6 months or, preferably, up to 4 months after birth, 3'-Siallylactose (3'-SL) and 6'-Siallylactose (6'-SL) are preferably administered in an amount effective to provide from 350 mg to 430 mg, from 380 mg to 400 mg, or from 390 mg to 395 mg of N-Acetyl-neuraminic acid (Neu5Ac) per kg body weight per day, such as in an amount effective to provide 393 mg of N-Acetyl-neuraminic acid (Neu5Ac) per kg body weight per day.

The daily dosage of 3'-Siallylactose (3'-SL) and 6'-Siallylactose (6'-SL) may be split up into at least two, preferably at least three, and most preferably into four portions, such that 3'-Siallylactose (3'-SL) and 6'-Siallylactose (6'-SL) are used or administered to an individual at least twice a day, preferably at least three times a day, and most preferably four times a day. It is particularly preferred that the daily dosage of 3'-Siallylactose (3'-SL) and 6'-Siallylactose (6'-SL) is split up into equal portions and/or that their use or administration is uniformly distributed throughout the day. For example, if the daily dosage of 3'-Siallylactose (3'-SL)

and 6'-Siallylactose (6'-SL) is split up into four equal portions and distributed uniformly throughout the day, then 25% of said dosage is used or administered to the individual after 0, 4, 8 and 12 hours.

Providing 3'-Siallylactose (3'-SL) and 6'-Siallylactose (6'-SL) to an individual in the herein specified amounts and time periods particularly addresses the needs of an infant of a given age and advantageously mimics the evolving nutritional quality and composition of breast milk during the lactation period.

More specifically, the herein described dosage regimen advantageously provides optimal supply of an infant with sialic acid in the form of sialyllactose and N-Acetylneuraminic acid (Neu5Ac) over time. Consequently, said regimen provides optimal nutritional support for the developing brain of an infant.

By optimizing of the sialic acid (Neu5Ac) concentration in the brain of said individual, particularly in the hippocampus and/or the frontal cortex of said individual, the herein described dosage regimen further ensures an optimized brain development including the development of learning skills and memory functions in the infant, as well as functions of perception, motor control, self-awareness, cognitive functioning and/or interpersonal experience.

In the context of the present invention, 3'-SL and 6'-SL may preferably be used or administered to an individual in the form of a nutritional composition as disclosed herein.

Therefore, the invention also refers to the use of 3'-SL and 6'-SL in the preparation of a nutritional composition for enhancing learning skills and/or enhancing memory function in an individual by increasing the sialic acid (Neu5Ac) concentration in the brain of said individual, particularly in the hippocampus and/or the frontal cortex of said individual. Said nutritional composition preferably corresponds to the nutritional composition of the present invention as disclosed herein.

Likewise, the expressions "dietary sialyllactose administration" and "dietary sialyllactose supplementation" preferably refer to the administration of 3'-SL and 6'-SL to an individual in the form of a nutritional composition as disclosed herein.

Nutritional Composition

The nutritional composition of the present invention can contain from 0.05 to 5 g of sialyllactose per 100 g of composition on a dry weight basis, e.g. from 0.1 to 2 g or from 0.2 to 1 g of sialyllactose per 100 g of composition on a dry weight basis.

In particular examples the composition comprises from 50 mg to 2500 mg of total sialyllactose per L of the nutritional composition, from 60 mg to 2000 mg of total sialyllactose per L of the nutritional composition, or from 80 mg to 1000 mg of total sialyllactose per L of the nutritional composition. In a particular embodiment, the composition comprises 2090 mg of total sialyllactose per L of composition. In another particular embodiment the composition comprises from 87.5 mg to 735 mg of total sialyllactose per L of the nutritional composition.

The nutritional composition of the present invention preferably comprises sialic acid oligosaccharides in the form of a combination of 3'-Siallylactose (3'-SL) and 6'-Siallylactose (6'-SL).

Accordingly, as used herein, "sialyllactose" refers to both, 3'-sialyllactose (3'-SL) and 6'-sialyllactose (6'-SL). The expression "total sialyllactose" means to the total quantity of both, 3'-Siallylactose (3'-SL) and 6'-sialyllactose (6'-SL) in the nutritional composition.

Preferably, 3'-Siallylactose (3'-SL) and 6'-Siallylactose (6'-SL) are comprised in said nutritional composition in a weight ratio between 10:1 and 1:10, such as between 10:1 and 2:1, between 8:1 and 3:1, between 6:1 and 3:1, between 5:1 and 3:1, between 5:1 and 4:1, or between 4.7:1 and 4.1:1. In a particular embodiment, 3'-Siallylactose (3'-SL) and 6'-Siallylactose (6'-SL) are comprised in the present nutritional composition in a weight ratio of 4.4:1.

In another particular embodiment, 3'-Siallylactose (3'-SL) and 6'-Siallylactose (6'-SL) are comprised in the nutritional composition of the invention in a weight ratio between 6:1 and 1:10, between 5.9:1 and 1.5:10, or between 5.86:1 and 1.53:10, and most preferably in a weight ratio of 1:1. In this embodiment, the individual is preferably a human such as human infant or a young child.

Further, in an embodiment, 3'-Siallylactose (3'-SL) and 6'-Siallylactose (6'-SL) may be comprised in the nutritional composition in an amount effective to provide from 110 mg to 180 mg, from 120 mg to 170 mg, or from 125 mg to 165 mg of total sialyllactose per kg body weight per day. In an embodiment, 3'-Siallylactose (3'-SL) and 6'-Siallylactose (6'-SL) may be comprised in the nutritional composition in an amount effective to provide 131 mg or 162 mg of total sialyllactose per kg body weight per day.

Further, 3'-Siallylactose (3'-SL) and 6'-Siallylactose (6'-SL) may be comprised in the nutritional composition in an amount corresponding to from 350 mg to 530 mg, from 380 mg to 500 mg, or from 390 mg to 490 mg of N-Acetylneuraminic acid (Neu5Ac) per kg body weight per day. In an embodiment, 3'-Siallylactose (3'-SL) and 6'-Siallylactose (6'-SL) may be comprised in the nutritional composition in an amount corresponding to 393 mg or 487 mg of N-Acetylneuraminic acid (Neu5Ac) per kg body weight per day.

As used herein, the expressions "composition(s)" and "nutritional composition(s)" are sought to refer to the nutritional composition for use in the present invention.

In the present context, a nutritional composition may be any kind of composition that provides a nutritional benefit to an individual and that may be safely consumed by a human or animal. It may be in solid, semi-solid or liquid form and may comprise one or more macronutrients, micronutrients, food additives, water, etc.

Generally, the nutritional composition may be in the form of a nutritional product, preferably a food product, a nutritional supplement, a full meal, a nutritionally complete formula, a pharmaceutical formulation, a functional food product, a beverage product, and combinations thereof.

In the context of the present invention, "nutritional product" encompasses any kind of ready-to-consume nutritional composition that provides a nutritional benefit to an individual, such as a food product, but any kind of nutritional composition to be reconstituted with a liquid (e.g. water, milk . . . ). In a particular embodiment, the nutritional product is a yogurt, juice, or a cereal bar.

The term "food product", as used herein, may be in solid, semi-solid or liquid form and may comprise one or more nutrients, foods or nutritional supplements. For instance, the food product may additional comprise the following nutrients and micronutrients: a source of proteins, a source of lipids, a source of carbohydrates, vitamins and minerals. The product may also contain anti-oxidants, stabilizers (when provided in solid form) or emulsifiers (when provided in liquid form).

The term "nutritional supplement" as used herein is to be understood as relating to a nutritional product that provides nutrients to an individual that may otherwise not be consumed in sufficient quantities by said individual. For instance, a nutritional supplement may include vitamins, minerals, fiber, fatty acids, or amino acids.

In the context of the present invention, the term "functional food product" is to be understood as a food product providing an additional health-promoting or disease-preventing function to the individual. Any kind of known biologically-active compounds may be added to the food product of the invention in order to provide additional health benefits.

A "pharmaceutical formulation" is to be understood as encompassing any pharmaceutically active substance in combination with a pharmaceutical carrier. The term may include any enteral or parenteral formulations such as tablets, capsules, oral liquids and injectibles. In addition to the active substance a pharmaceutical formulation may contain solubilizers, stabilizers, buffers, tonicity modifiers, bulking agents, viscosity enhancers/reducers, surfactants, chelating agents, and adjuvants.

Preferably, the nutritional composition of the invention is an infant formula, such as a starter infant formula, a follow-on formula or a preterm infant formula, a milk fortifier such as a human milk fortifier, a baby food formula, a growing-up milk, an infant cereal composition, a medical food product for clinical nutrition or a supplement.

In a particularly preferred embodiment the nutritional composition is an infant formula, a human milk fortifier, or a supplement.

The term "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

Generally a "starter infant formula" is intended for infants from birth as breast-milk substitute.

A "follow-up formula" or "follow-on formula" is given from the 6th month onwards. It constitutes the principal liquid element in the progressively diversified diet of this category of person.

The term "preterm infant formula" means an infant formula intended for a preterm infant.

The term "milk fortifier" refers to liquid or solid nutritional compositions suitable for mixing with breast milk (which is human milk for a human milk fortifier) or infant formula. It is used to increase the calories, protein, minerals and vitamins in breast milk fed to preterm infants or infants with a low birth weight. The term "breast milk" is to be understood as the mother's milk or the colostrum of the mother or a donor's milk or the colostrum of a donor's milk.

The term "baby food formula" means a foodstuff intended for particular nutritional use by infants or children such as young children, during the first years of life.

The "growing-up milk" (or GUM) is given from one year onwards. It is generally a milk-based beverage adapted for the specific nutritional needs of young children.

The expression "infant cereal composition" means a foodstuff intended for particular nutritional use by infants or children such as young children, during the first years of life.

A "medical food product for clinical nutrition" or "medical food" is to be understood as a food which is formulated to be consumed or administered enterally under the supervision of a physician and which is intended for the specific dietary management of a disease or condition for which distinctive nutritional requirements, based on recognized scientific principles, are established by medical evaluation.

A "supplement" (or a "complement") is typically to be used during hospital stay and/or to be used after hospital discharge. A supplement can be for a preterm infant or a child or an adult. Said supplement is preferably a product for preterm feeding such as a preterm infant formula, a human milk fortifier, or a preterm infant supplement. It may be in the form of powder, tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

In a preferred embodiment, the supplement may be added to human breast milk that is naturally derived from the infant's mother.

The supplement may also be added in a product acceptable to the infant, such as an ingestible carrier or support, respectively. Examples of such carriers or supports are pharmaceutical compositions, food compositions or pet food compositions. Non-limiting examples for such compositions are milk, yogurt, curd, cheese, fermented milks, milk based fermented products, fermented cereal based products, milk based powders, human milk, infant formula, preterm infant formula, starter infant formula, follow-on formula, baby food formula, a medical food product for clinical nutrition, oral supplement, and tube feeding. Further, the supplement may contain an organic or inorganic carrier material suitable for enteral or parenteral administration as well as vitamins, minerals trace elements and other micronutrients in accordance with the recommendations of Government bodies such as the USRDA.

In a preferred embodiment, the nutritional composition of the present invention is a synthetic nutritional composition (i.e. not breast milk). The expression "synthetic nutritional composition" means a synthetic mixture obtained by chemical and/or biological means, which may be chemically identical to the mixture naturally occurring in mammalian milks.

The herein described nutritional composition may be used in an individual as the only feeding source or in addition to breast feeding.

Further, the herein described nutritional composition can also be a product for children or adults such as yogurt or medical food, as well as a pet food product.

Generally, a nutritional composition as described herein may comprise the following macronutrients: a source of proteins, a source of lipids, a source of carbohydrates and any combination thereof.

Furthermore, the nutritional composition may comprise the following micronutrients: vitamins, minerals, fiber, phytochemicals, antioxidants, prebiotics, probiotics, and any combination thereof. The composition may also contain food additives such as stabilizers (when provided in solid form) or emulsifiers (when provided in liquid form).

The nutritional composition may contain a protein source.

The protein can be in an amount of from 1.2 to 3 g per 100 kcal, such as from 1.5 to 2.0 g per 100 kcal, such as below 2.0 g per 100 kcal, e.g. between 1.8 to 2 g per 100 kcal, or in an amount below 1.8 g per 100 kcal such as from 1.4 to 1.7 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed. In one particular embodiment the proteins of the composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

The nutritional composition may further contain a carbohydrate source. This is particularly preferable in the case where the nutritional composition of the invention is an infant formula. In this case, any carbohydrate source conventionally found in infant formulae such as lactose, sucrose, maltodextrin, starch and mixtures thereof may be used although one of the preferred sources of carbohydrates is lactose.

The nutritional composition may further contain a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition may contain emulsifiers and stabilisers such as soy, lecithin, citric acid esters of mono- and diglycerides, and the like.

The nutritional composition may also contain probiotics. The term "probiotic" means microbial cell preparations or components of microbial cells with a beneficial effect on the health or well-being of the host. (Salminen S, Ouwehand A. Benno Y. et al. "Probiotics: how should they be defined" Trends Food Sci. Technol. 1999:10 107-10). The microbial cells are generally bacteria or yeasts.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp. In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut RoseII (Lallemand) under the trademark R0070.

The nutritional composition may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition can further comprise at least one non-digestible oligosaccharide (e.g. prebiotics) other than the sialylated oligosaccharides previously mentioned. Examples of prebiotics include certain oligosaccharides, such as fructooligosaccharides (FOS), galactooligosaccharides (GOS), fucosylated oligosaccharides (such as 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof), N-acetylated oligosaccharides (such as lacto-N-tetraose (LNT), N-neotetraose (LNnT) and any combination thereof). They could be usually in an amount between 0.3 and 10% by weight of composition.

Use of the Nutritional Composition

The present nutritional composition may be used in enhancing learning skills and/or enhancing memory function in an individual, by increasing the sialic acid (Neu5Ac) concentration in the brain of said individual. The present nutritional composition may be used to increase the sialic acid (Neu5Ac) concentration in the brain of said individual, especially to the sialic acid (Neu5Ac) concentration in the hippocampus and/or frontal cortex. Said use in enhancing memory function of an individual preferably comprises enhancing short-term memory function or long-term memory function, and, more preferably, both short-term memory function and long-term memory function.

More specifically, said nutritional composition may be used in enhancing learning skills and/or enhancing memory function in an individual, by increasing the sialic acid (Neu5Ac) concentration in a brain region selected from hippocampus, frontal cortex, or a combination thereof, and preferably in hippocampus.

Furthermore, the present nutritional composition may be used in enhancing learning skills and/or enhancing memory function in an individual, by enhancing neuroplasticity in the brain of an individual. The present nutritional composition may be used to enhance neuroplasticity in the brain of an individual.

Moreover, the present nutritional composition may be used in enhancing learning skills and/or enhancing memory function in an individual, by enhancing neurodevelopment, myelination, neurogenesis, axonal sprouting and/or maturation in the brain of said individual.

It may also be used in enhancing functions of perception, motor control, self-awareness, cognitive functioning and/or interpersonal experience in an individual.

It may also be used to increase of the grey matter volume in the region of Insular cortex, Somatosensory cortex, Parahippocampal, Superior temporal and/or Cerebellar lobule in the brain of said individual.

Preferably, the present nutritional composition is used in a mammal, preferably in a pet or a human, and more preferably in a human.

In a particularly preferred embodiment, the present nutritional composition is used in an infant, a young child, a child, a teenager or an adult, and more preferably in an infant or a young child. In a particular embodiment, the present nutritional composition is used in a formula-fed infant.

The present nutritional composition may further be used in an individual who is preterm, a small for gestational age (SGA) and/or a low birth weight (LBW), such as in a preterm infant, a small for gestational age (SGA) infant and/or a low birth weight (LBW) infant.

Preferably, the present nutritional composition may be used in an individual during the early age of said individual, and particularly during the infant phase of said individual, i.e. during the first 12 months after birth. Even more preferably, the nutritional composition is used in an individual during the first 8 months after birth, or during the first 6 months after birth, and preferably during the first 4 months after birth, or during the first 2 months after birth. The expressions "x months after birth", "x months of birth" and "X months of age" can be used alternatively. The nutritional composition of the invention can be administered (provided, fed . . . ) during the entire time window (e.g. from birth up to 2, 4 or 6 months) or only a part thereof (e.g. from 1, 2, 3 or 4 weeks after birth up to 1, 3 or 5 months). In addition, the nutritional composition can be administered continuously (i.e. at every meal of the infant/young child) or not. In some advantageous embodiments of the invention, the nutritional composition is administered during their entire specific window of time and/or continuously.

The nutritional composition may be administered to an individual in an amount effective to provide from 110 mg to 180 mg, from 120 mg to 170 mg, or from 125 mg to 165 mg of total sialyllactose per kg body weight per day. In an embodiment, the nutritional composition may be administered in an amount effective to provide 131 mg or 162 mg of total sialyllactose per kg body weight per day.

In a particular embodiment, the nutritional composition is administered to an individual during the first two weeks after birth in an amount effective to provide from 140 mg to 180 mg, from 150 mg to 170 mg, or from 160 mg to 165 mg of total sialyllactose per kg body weight per day, such as in an amount of 162 mg of total sialyllactose per kg body weight per day, From two weeks after birth and up to 12 months after birth, such as up to 8 months, up to 6 months or, preferably, up to 4 months after birth, or up to 2 months after birth, the nutritional composition is preferably administered in an amount effective to provide and from 110 mg to 150 mg, from 120 mg to 140 mg, or from 125 mg to 135 mg of total sialyllactose per kg body weight per day, such as in an amount effective to provide 131 mg of total sialyllactose per kg body weight per day.

It is further preferred that the nutritional composition is administered to an individual in an amount corresponding to from 350 mg to 530 mg, from 380 mg to 500 mg, or from 390 mg to 490 mg of N-Acetyl-neuraminic acid (Neu5Ac) per kg body weight per day, such as in an amount corresponding to 393 mg of N-Acetyl-neuraminic acid (Neu5Ac) per kg body weight per day, or in an amount corresponding to 487 mg of N-Acetyl-neuraminic acid (Neu5Ac) per kg body weight per day.

In a particular embodiment, the nutritional composition is administered to an individual during the first two weeks after birth in an amount corresponding to from 450 mg to 530 mg, from 480 mg to 500 mg, or from 485 mg to 490 mg per kg body weight per day, such as in an amount corresponding to 487 mg of N-Acetyl-neuraminic acid (Neu5Ac) per kg body weight per day, From two weeks after birth and up to 12 months after birth, such as up to 8 months, up to 6 months or, preferably, up to 4 months after birth, or up to 2 months after birth, the nutritional composition is preferably administered in an amount effective to provide from 350 mg to 430 mg, from 380 mg to 400 mg, or from 390 mg to 395 mg of N-Acetyl-neuraminic acid (Neu5Ac) per kg body weight per day, such as in an amount effective to provide 393 mg of N-Acetyl-neuraminic acid (Neu5Ac) per kg body weight per day.

Further, the nutritional composition of the invention may be administered such that the daily dosage of 3'-Siallylactose (3'-SL) and 6'-Siallylactose (6'-SL) may be split up into at least two, preferably at least three, and most preferably into four portions, such that the nutritional composition is used in or administered to an individual at least twice a day, preferably at least three times a day, and most preferably four times a day. It is particularly preferred that the nutritional composition of the invention is administered such that the daily dosage of 3'-Siallylactose (3'-SL) and 6'-Siallylactose (6'-SL) is split up into equal portions and/or that the use or administration of the nutritional composition of the invention is uniformly distributed throughout the day. For example, if the daily dosage of 3'-Siallylactose (3'-SL) and 6'-Siallylactose (6'-SL) is to be split up into four equal portions and distributed uniformly throughout the day, then an amount of the nutritional composition comprising or corresponding to 25% of said daily dosage of 3'-Siallylactose (3'-SL) and 6'-Siallylactose (6'-SL) is to be used in or administered to the individual after 0, 4, 8 and 12 hours.

Administering the nutritional composition of the invention in the herein specified amounts and time periods advantageously provides optimal supply of an infant with sialic acid in the form of sialyllactose and N-Acetyl-neuraminic acid (Neu5Ac) over time. Consequently, optimal nutritional support is provided for the developing brain of an infant in that the sialic acid (Neu5Ac) concentration in the brain of said infant, and particularly in the hippocampus and/or the frontal cortex of said infant, are optimized.

Therefore, administering the nutritional composition of the invention in the herein specified amounts and time periods further improves brain development, learning skills and memory functions, and functions of perception, motor control, self-awareness, cognitive functioning and/or interpersonal experience in the infant.

Generally, the nutritional composition of the invention may be used in the individual as the only feeding source or in addition to breast feeding, such as in the form of an infant formula, a preterm infant formula, a human milk fortifier, a starter infant formula, a follow-on formula, a baby food formula, a growing-up milk, an infant cereal composition, a medical food product for clinical nutrition or a supplement.

Method for Manufacturing the Nutritional Composition

The nutritional composition may be prepared in any suitable manner known in the art.

For example, it may be prepared by blending together a protein source, a carbohydrate source (different from the oligosaccharide combination of the present invention), and a fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50[deg.]C. and about 80[deg.]C. to aid dispersal of the ingredients. Commercially available liquefiers may be used to form the liquid mixture. The 3'-Siallylactose (3'-SL) and 6'-Siallylactose (6'-SL) will be added at this stage if the final product is to have a liquid form. If the final product is to be a powder, the 3'-Siallylactose (3'-SL) and 6'-Siallylactose (6'-SL) may likewise be added at this stage if desired. The liquid mixture is then homogenised, for example in two stages.

The liquid mixture may then be thermally treated to reduce bacterial loads, by rapidly heating the liquid mixture to a temperature in the range between about 80[deg.]C. and about 150[deg.]C. for a duration between about 5 seconds and about 5 minutes, for example. This may be carried out by means of steam injection, an autoclave or a heat exchanger, for example a plate heat exchanger. Then, the liquid mixture may be cooled to between about 60[deg.]C. and about 85[deg.]C., for example by flash cooling. The liquid mixture may then be again homogenized, for example in two stages between about 10 MPa and about 30 MPa in the first stage and between about 2 MPa and about 10 MPa in the second stage. The homogenized mixture may then be further cooled to add any heat sensitive components, such as vitamins and minerals. The pH and solids content of the homogenized mixture are conveniently adjusted at this point. The homogenized mixture is transferred to a suitable drying apparatus such as a spray dryer or freeze dryer and converted to powder. The powder should have a moisture content of less than about 5% by weight.

3'-Siallylactose (3'-SL) and 6'-Siallylactose (6'-SL) may be added at this stage by dry-mixing, or by blending them in a syrup form of crystals and spray-dry (or freeze-dry).

In the present method, 3'-Siallylactose (3'-SL) and 6'-Siallylactose (6'-SL) are preferably added in a weight ratio between 10:1 and 1:10, such as between 10:1 and 2:1, between 8:1 and 3:1, between 6:1 and 3:1, between 5:1 and 3:1, between 5:1 and 4:1, or between 4.7:1 and 4.1:1. In a particular embodiment, 3'-Siallylactose (3'-SL) and 6'-Siallylactose (6'-SL) are added in a weight ratio of 4.4:1.

In another particular embodiment, 3'-Siallylactose (3'-SL) and 6'-Siallylactose (6'-SL) are added in a weight ratio between 6:1 and 1:10, between 5.9:1 and 1.5:10, or between 5.86:1 and 1.53:10, and most preferably in a weight ratio of 1:1. In this embodiment, the nutritional composition is preferably for a human such as human infant or a young child.

If a liquid composition is preferred, the homogenized mixture may be sterilized then aseptically filled into suitable containers or may be first filled into the containers and then retorted.

The present invention is further illustrated herein by means of the following non-limiting examples.

EXAMPLES

Example 1: Nutritional Composition Comprising 3'-Siallylactose (3'-SL) and 6'-Siallylactose (6'-SL)

A nutritional composition comprising 3'-Siallylactose (3'-SL) and 6'-Siallylactose (6'-SL) is given in Table 1 below. This composition is given by way of illustration only.

TABLE 1

| Nutrients | per 100 kcal | per liter |
| --- | --- | --- |
| Energy (kcal) | 100 | 670 |
| Proteins (g) | 1.83 | 12.3 |
| Fats (g) | 5.3 | 35.7 |
| Linoleic acid (g) | 0.79 | 5.3 |
| α-Linolenic acid (mg) | 101 | 675 |

TABLE 1-continued

| Nutrients | per 100 kcal | per liter |
|---|---|---|
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| 3'-SL (g) | 0.22 | 1.46 |
| 6'-SL (g) | 0.05 | 0.33 |
| Ratio 3'-SL:6'-SL | 4.4:1 | 4.4:1 |

Example 2: Effects of a Dietary Sialic Acid Supplementation on Learning Skills

The following study was performed to investigate the effects of a dietary sialic acid in both protein-bound and oligosaccharide-bound form, and the combination of sialic acid and lactoferrin, on the learning performance in newborn piglets.

Animal Model

Three-day-old full term healthy male domestic piglets (Sus scrofa, Landrace×Large White cross) were purchased from a commercial piggery. The pig model was chosen since the potential for using pigs in pediatric brain research was recognized early more than 40 years ago, due to the similarities in the whole brain growth at the time of birth, the gross anatomy, the growth pattern of neonatal brain to that of human. The pig digestive system shares similar physiology and anatomical structure with human infants and has comparable nutrient requirement. These make piglets ideally suited for the coordinated nutritional, metabolic and molecular investigation. The pig has the potential to fill the gap between preclinical studies with rodents and clinical trials in humans.

Study Design

All piglets were obtained from a commercial piggery in Xiamen, China. Male domestic piglets (Sus scrofa, Landrace×Large White F1) were obtained at 3 days of age. For each trial, 2 piglets living in one home pen came from different litters. The piglets from the same litter were averagely distributed to each group randomly. All animals were kept in the temperature-controlled environment with a 12 h light (08:00-20:00) and a 12 h dark (20:00-08:00) cycle. The home pens contained a "nest" (a rubber tire covered with a clean towel), a heat lamp over the nest and an identical woody toy hang in the home pen. All facilities (including home pens and behavior room) were monitored for 24 h. The feeding time was fixed as 8:00, 13:00, 18:00, 22:30, with an extra 50 mL milk/pig supplied at the last feeding.

The piglets were fed a standard sow milk-replacer containing proteins from soy/whey/casein (50:38:12) (Milk 1) and the test milks (Milks 2-4) from 3 days of age to 38 days of age. For each of the test milks, 180 g milk powder was reconstituted with water to provide 1 L (1000 ml) of test milk.

The test milk of the "Sialyl core 1" treatment group was supplemented with 3.84 g casein-glycomacropeptide (cGMP) per 100 g milk powder (Milk 2).

The test milk of the "Sialyllactose" treatment group comprised 1.16 g of a mixture of 3'-sialyllactose (3'-SL) and 6'-sialyllactose (6'-SL) per 100 g milk powder, said mixture comprising 3'SL in a concentration of 81.6% per weight of said mixture (0.95 g of 3'SL per 100 g powder) and 6'SL in a concentration of 18.4% per weight of said mixture (0.21 g of 6'SL per 100 g powder) to give a 3'SL/6'SL ratio of 4.4:1 (Milk 3).

The test milk of the "Sialyl core 1+sialyllactose+Lactoferrin" treatment group was supplemented with 1.12 g casein-glycomacropeptide (cGMP), 0.58 g 3'-Sialyllactose and 0.28 g lactoferrin (LF) per 100 g of the milk powder (Milk 4).

The final concentrations of N-acetylneuraminic acid and N-Glycolylneuraminic Acid in the milks of control and treatment groups are given in Table 2 below. The data provided in Table 2 was obtained from an analysis of the readily prepared test milk products, i.e. of the control (Milk 1) and the control after supplementation with casein-glycomacropeptide (cGMP) (Milk 2: "Sialyl core 1"), 3'-Sialyllactose/6'-Sialyllactose (Milk 3: "Sialyllactose"), and cGMP/3'-Sialyllactose/lactoferrin (LF) (Milk 4: "Sialyl core 1+sialyllactose+Lactoferrin"),

TABLE 2

| | | Sialic Acid (mg/100 g) | | | |
|---|---|---|---|---|---|
| Group | | N-Acetylneuraminic Acid (Neu5Ac) | | N-Glycolylneuraminic Acid (Neu5Gc) | |
| Control | (Milk 1) | 78.8 / 76.5 | 77.7 ± 1.6 | 2 / 2 | 2.0 ± 0 |
| Sialyl core 1 | (Milk 2) | 574.7 / 628.8 | 601.8 ± 38.3 | 5.5 / 6 | 5.8 ± 0.4 |
| Sialyllactose | (Milk 3) | 461.9 / 511.7 | 486.8 ± 35.2 | 2.6 / 2.1 | 2.4 ± 0.4 |
| Sialyl core 1 + sialyllactose + Lactoferrin | (Milk 4) | 416.3 / 461.9 | 439.1 ± 32.2 | 3.2 / 3.4 | 3.3 ± 0.1 |

The pig milk replacers were formulated so that total carbohydrates intake remained the same irrespective of the amount of added N-acetylneuraminic acid. To maintain normal rates of growth, the piglets received 285 mL milk/kg body/day in the first 2 weeks of the study and 230 mL/kg body/day in the remaining weeks. Body weight, milk intake, and health status of piglets were recorded daily. All piglets in the control and treatment groups were exposed to learning challenges.

Learning and Memory Test Using 8-Arm Radial Maze

All piglets were introduced into an 8-arm radial maze individually. Two tests were performed with each group: an 'easy' task and a more 'difficult' task (FIG. 1). Both tests had accessible milk in only one arm and inaccessible milk in the remaining 7 arms so that all arms have the same smells to prevent olfactory learning (FIG. 1). In both tests, a visual cue consisting of 3 black dots is placed randomly on a door with accessible milk (corresponding to their group milk) in the arm. In the easy task, 1 black dot visual cue is placed on the remaining 7 doors with inaccessible milk (the same amount and type milk as the accessible milk). In the difficult task, a visual cue with 2 black dots is placed on the remaining 7 doors. The position of 3 black dots visual cue was changed between trials in a predetermined random order. All piglets were to enter the maze individually. 80 trials for easy task and difficult task (40 each) were conducted over a 10-day period beginning when piglets were 22 days of age.

Assessment of learning capacity was determined based on the number of trials taken to successfully learn the visual cue. Learning was quantified using the number of mistakes and successes in finding the accessible milk arm during each trial. A mistake was recorded each time when the piglet entered or put its whole head through the wrong door. A success was recorded when the piglet entered the correct door. The criterion of learned the visual cues were: (A) a maximum of 1 mistake in 3 consecutive trials, (B) no mistakes in 3 consecutive trials, (C) a maximum of 1 mistake in 4 consecutive trials, (D) no mistakes in 4 consecutive trials, (E) a maximum of 1 mistake in 5 consecutive trials (F) no mistakes across 5 consecutive trials. An overhead video camera recorded continuously during the learning and memory test, and a trained observer simultaneously recorded the results manually. All the tests were conducted by trained staff blinded to the intervention information. Results were corroborated by independent analysis of the video material. To reduce stress and familiarize the piglets with the test protocol, we allowed two piglets from the same pen into the maze to learn how to open and close the door before the learning test (8 trials).

Results of Learning Performance of 8-Arm Radial Maze Learning Speed

Figure 2:
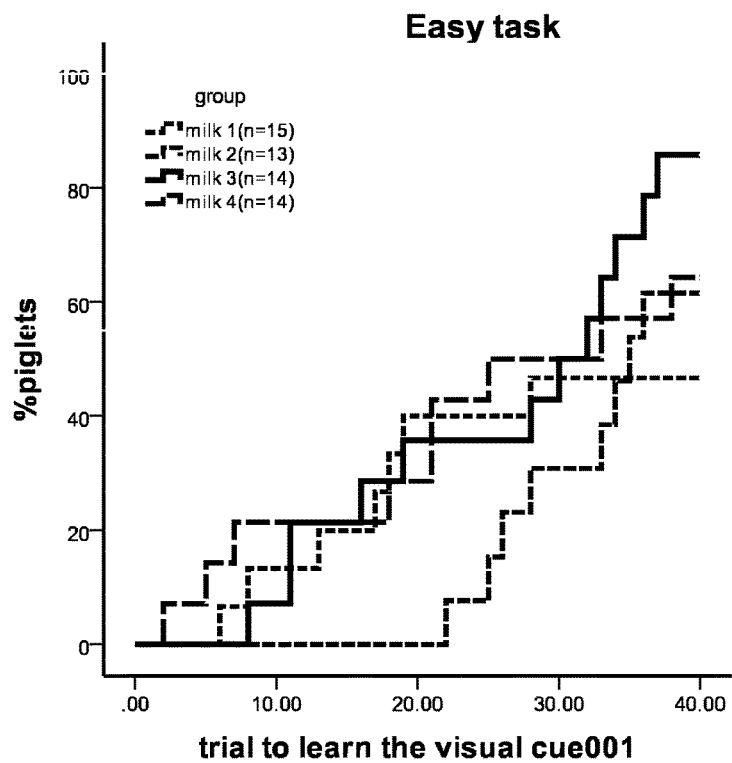
FIGS. 2A and 2B depict the results of Example 2 regarding learning speed after dietary sialic acid supplementation, wherein the total numbers of mistakes per day in the 8-arm radial maze test were analyzed.
Figure 2:
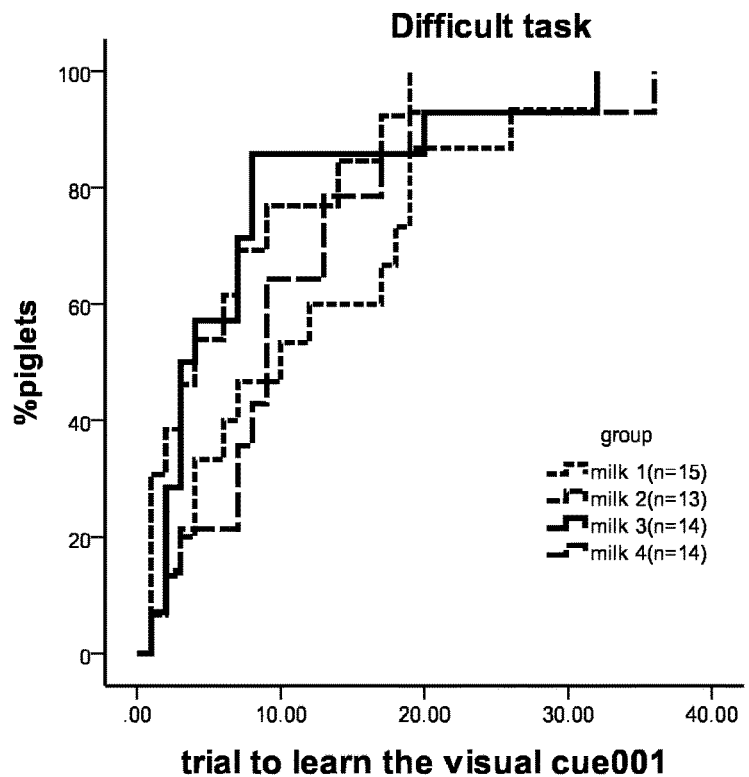

The maximum of 1 mistake across 3 consecutive trials was used as learning criterion. It was found that in both easy task and difficulty task, the sialyllactose group (i.e. Milk 3) learned the visual cue significantly faster than the other groups (i.e. Milk 1, Milk 2 and Milk 4 groups). Data were analyzed using the total number of mistakes as covariances for analysis ($P<0.01$ in both easy and difficulty tasks, Cox-regression, FIG. 2A and FIG. 2B).

Figure 3:
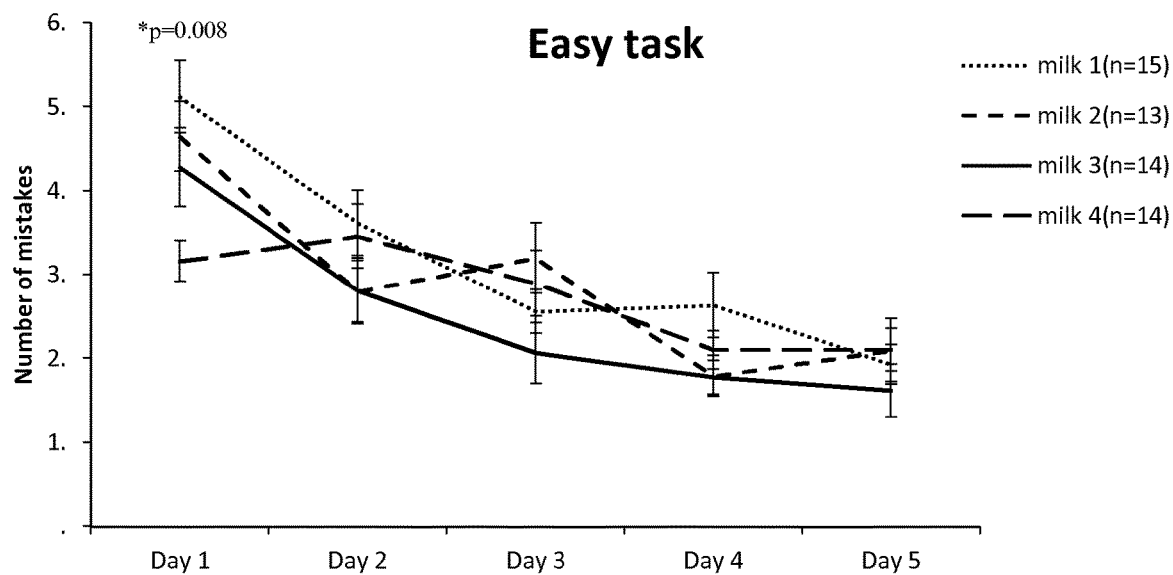
FIGS. 3A and 3B depict the results of Example 2 regarding learning speed after dietary sialic acid supplementation, wherein the mean numbers of mistakes per day in the 8-arm radial maze test were analyzed.
Figure 3:
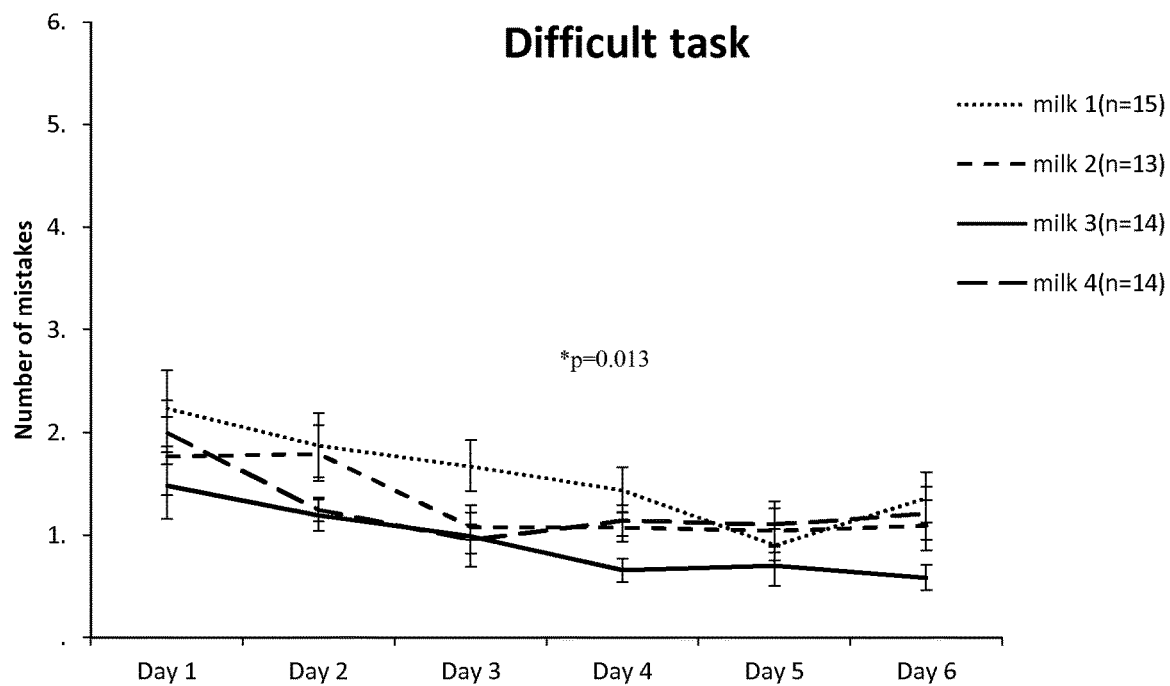

Since learning and memory functions of the piglets would improve during the training, also the mean numbers of mistakes per day were analyzed (FIGS. 3A and 3B). In the sialyllactose group (Milk 3) the mean number of mistakes was lower than that in the control group in both easy and difficult task throughout the trials, in particular on day 4 of training ($P<0.05$, Repeated measures). There was a significant difference in the total number of mistakes on day 1 for the easy task ($P<0.05$, One-way ANOVA, FIG. 3A) and on day 4 for the difficult task ($P<0.05$, One-way ANOVA, FIG. 3B).

Number of Mistakes and Success as a Measure of Learning

Figure 4:
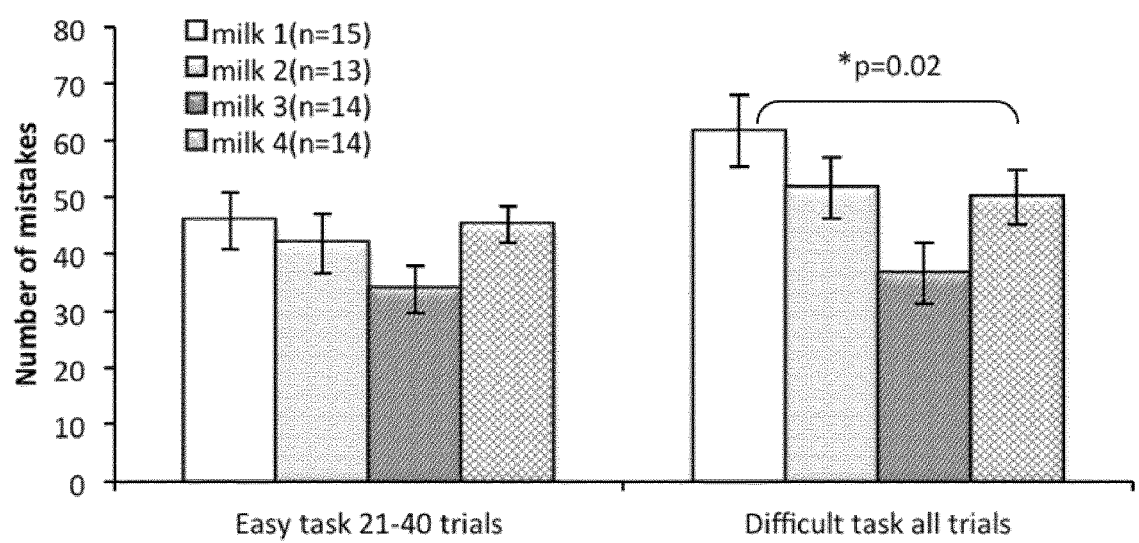
FIG. 4 depicts the results of Example 2 regarding the number of mistakes in the second half of the easy task (trials 21-40) and all 40 trials of the difficult task of the 8-arm radial maze test.

Further, the total number of mistakes was also considered as a covariate measure of learning, since learning in the first 20 trials of the easy task was likely to be predominantly "trial and error". Thus, the first 20 trials as covariates analyzed learning speed of the easy task. Trials 21-40 of the easy task and total number of mistakes were determined separately. The piglets of the sialyllactose group (Milk 3) were shown to make fewer mistakes than the other groups (Milk 1, Milk 2 and Milk 4 groups) in the easy task ($P=0.164$ for trials 21-40) and the difficulty task ($P=0.002$, One-way ANOVA, FIG. 4).

Figure 5:
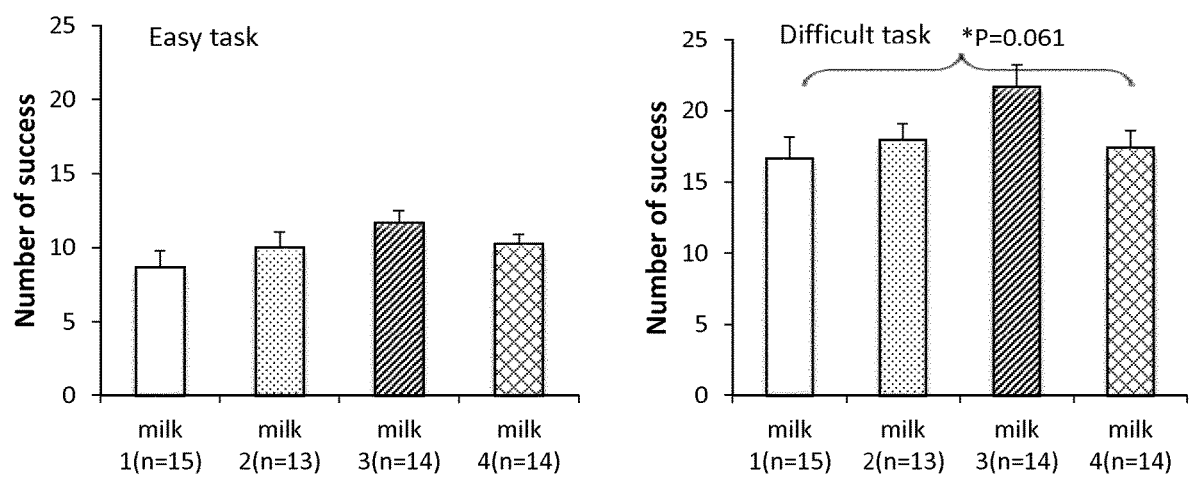
FIG. 5 depicts the results of Example 2 regarding the total number of success in 40 trials of the easy task and difficult task of the 8-arm radial maze test.

The total number of success was also considered as a measure of learning. The sialyllactose group (milk 3) piglets had a higher number of success than the other groups (control, milk 1, milk 2 and milk 4 groups) in both easy ($P=0.34$) and difficult task ($P=0.061$, FIG. 5).

Thus, a dietary supplementation with a combination of 3'-Sialyllactose and 6'-Sialyllactose in the inventive weight ratio of 4.4:1 was again demonstrated to improve learning performance in the developing piglets.

Number of Mistakes Made During Different Stages of Learning in the Easy and Difficult Learning Task Further, the total number of mistakes per 10 trials was analyzed separately. All piglets in the four groups had a learning improvement during 40 trials training. However, the piglets in the sialyllactose group (Milk 3) made a significantly lower number of mistakes than the piglets in the other groups (Milk 1, Milk 2 and Milk 4 groups) ($P<0.05$, repeated measures), in particular in trials 31-40 of the difficult task ($P<0.05$, general liner model ANOVA). Thus, a dietary supplementation with sialylated oligosaccharides (sialyllactose) was shown to reduce the total number of mistakes during learning.

Conclusion

The above results demonstrate that a dietary supplementation with a combination of 3'-Sialyllactose and 6'-Sialyllactose, especially in the inventive weight ratio of 4.4:1, significantly improves learning performance and enhances learning speed in the developing piglets. Further, it was shown that sialic acid in oligosaccharide bound form (sialyllactose) is more effective in improving learning performance and enhancing learning speed than sialic acid in protein-bound form (sialyl core 1). Furthermore, it was demonstrated that a combination of 3'-Sialyllactose and 6'-Sialyllactose as present in human breast milk is more effective in improving learning performance and enhancing learning speed than 3'-sialyllactose, even if the latter is combined with sialic acid in protein-bound form (sialyl core 1) and lactoferrin.

Example 3: Effects of a Dietary Sialic Acid Supplementation on Memory Functions

Subsequent to the assessment of learning skills described in Example 2, the effects of a dietary sialic acid supplementation on the short term memory (STM) and long-term memory (LTM) of the piglets was tested.

Memory Test

Two days after completion of each set of trials, the same task described in Example 2 was presented as a "memory test". Based on the time interval between the trials, piglet's "short-term memory" (STM) and "long-term memory" (LTM) were evaluated. There were four trials in the morning and four trials in the afternoon per day. Each piglet was tested in two consecutive trials. The intervention interval time for changing the visual cue and placing fresh milk between two trials was 5 minutes (corresponding to 5 minutes short term memory). During the 5 minutes period the piglet was located at the waiting zone outside the test zone. 40 minutes later (corresponding to 40 minutes long term memory), the piglet was introduced into the radial maze again for two further consecutive trials. The number of mistakes in finding the accessible milk is recorded as an index of memory.

Results of the Memory Test

Figure 6A:
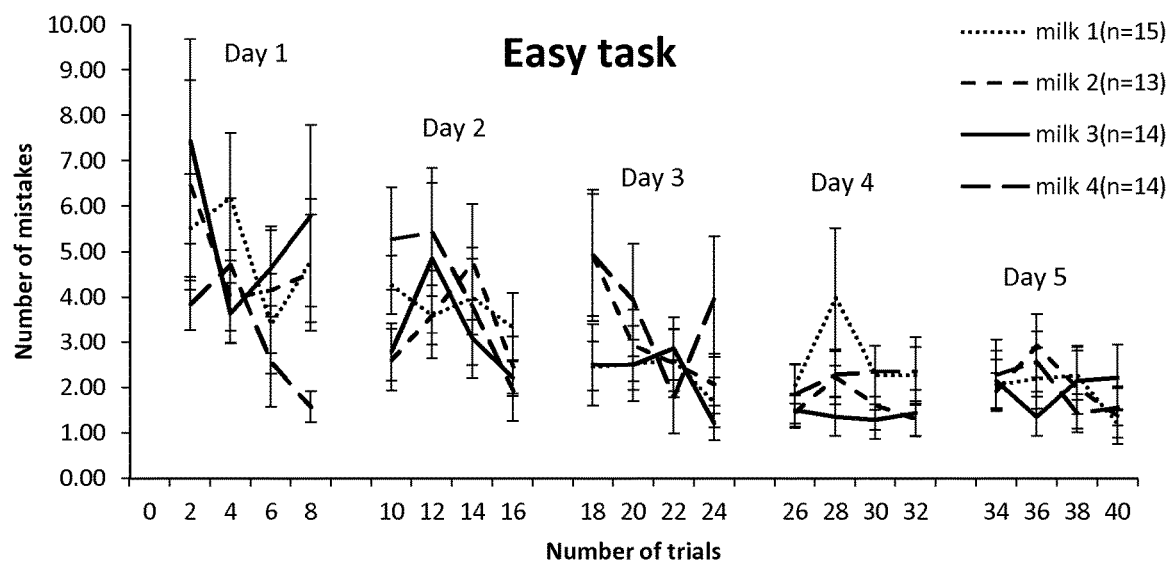
FIGS. 6A and 6B depict the results of Example 3 regarding short term memory (STM, FIG. 6A) and long-term memory function (LTM, FIG. 6B)
Figure 6B:
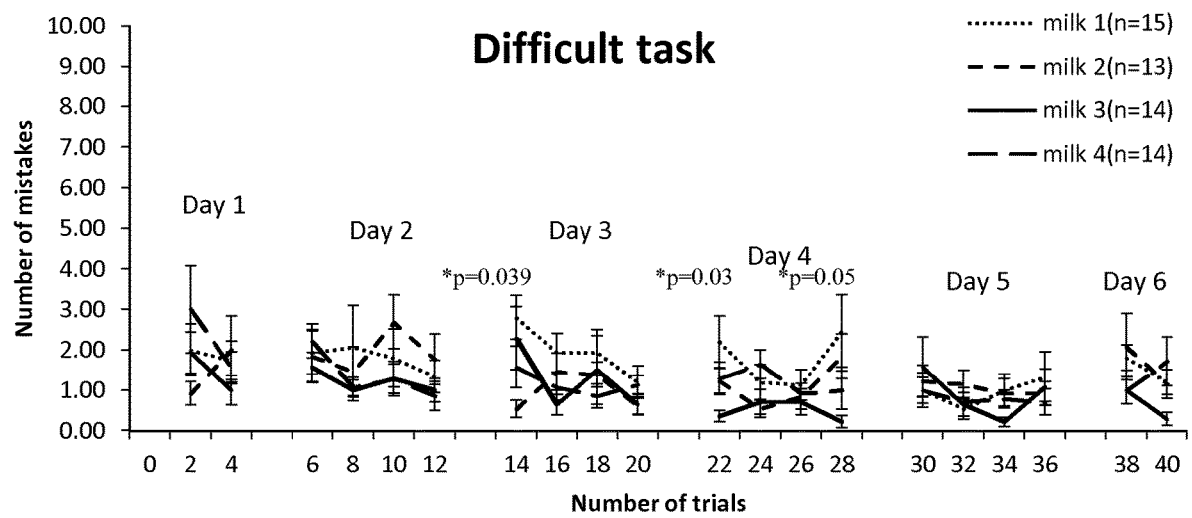
Figure 7A:
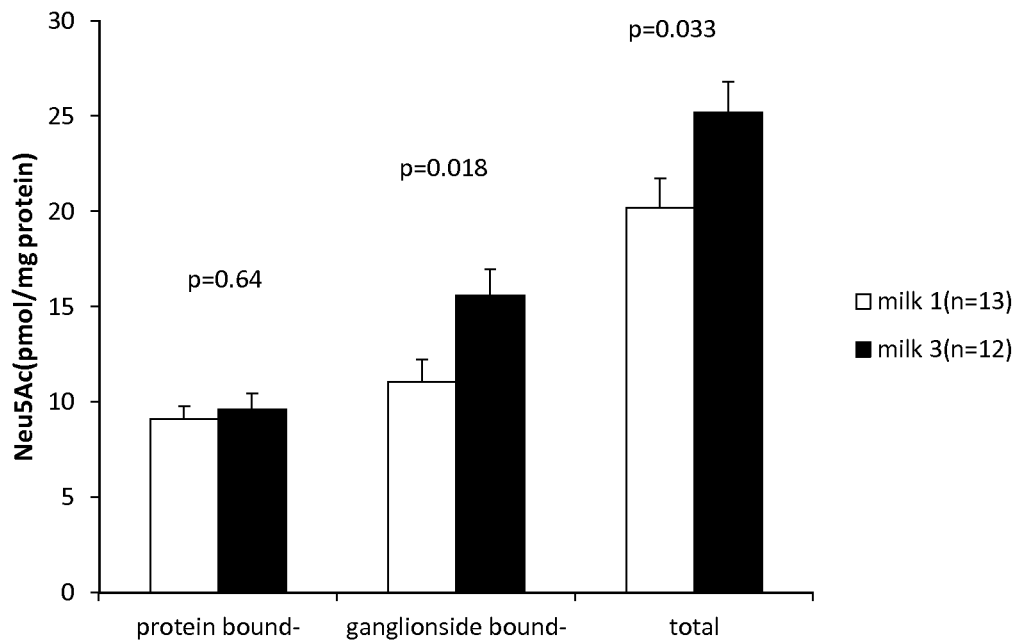
FIG. 7A-D depict the results of Example 4 regarding the sialic acid concentration in different brain regions after dietary sialic acid supplementation.
Figure 7B:
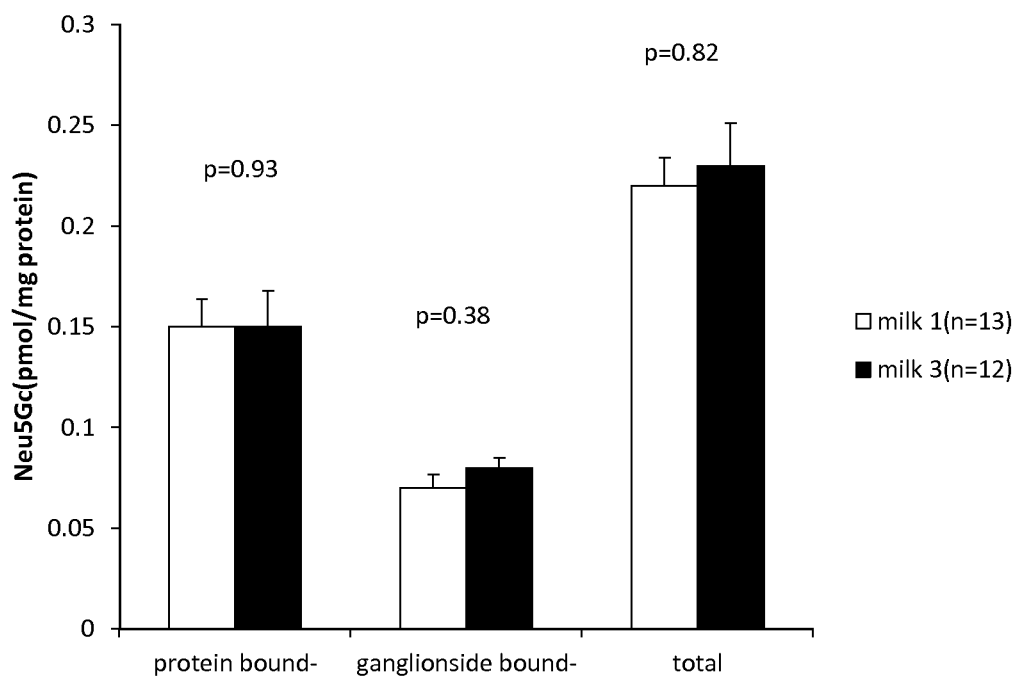
Figure 7C:
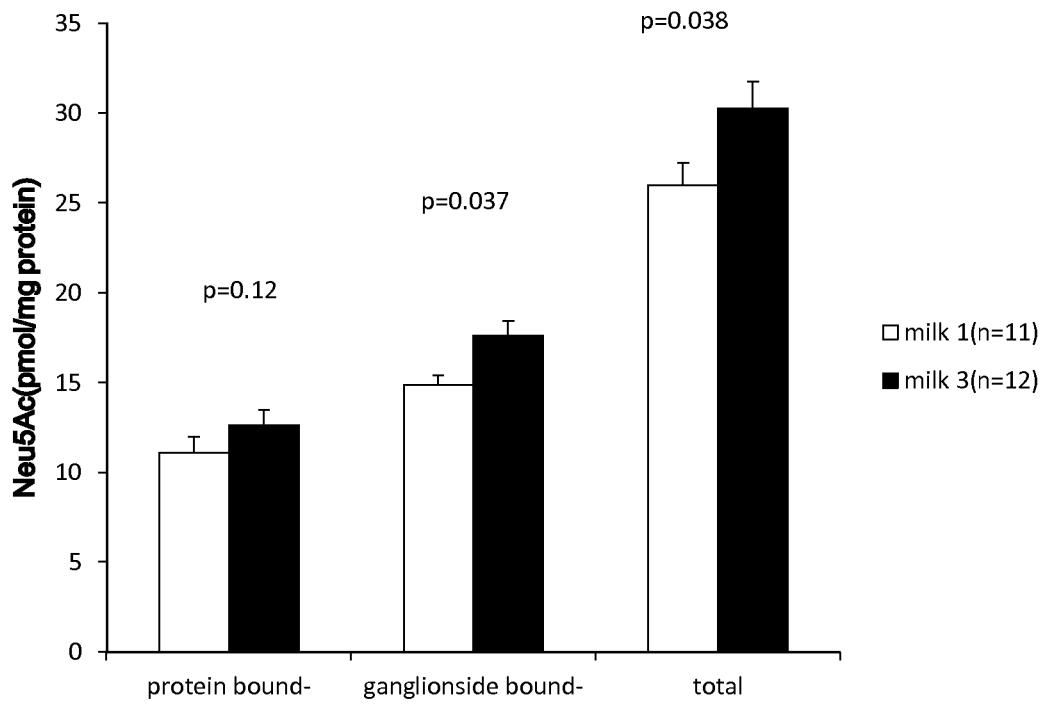
Figure 7D:
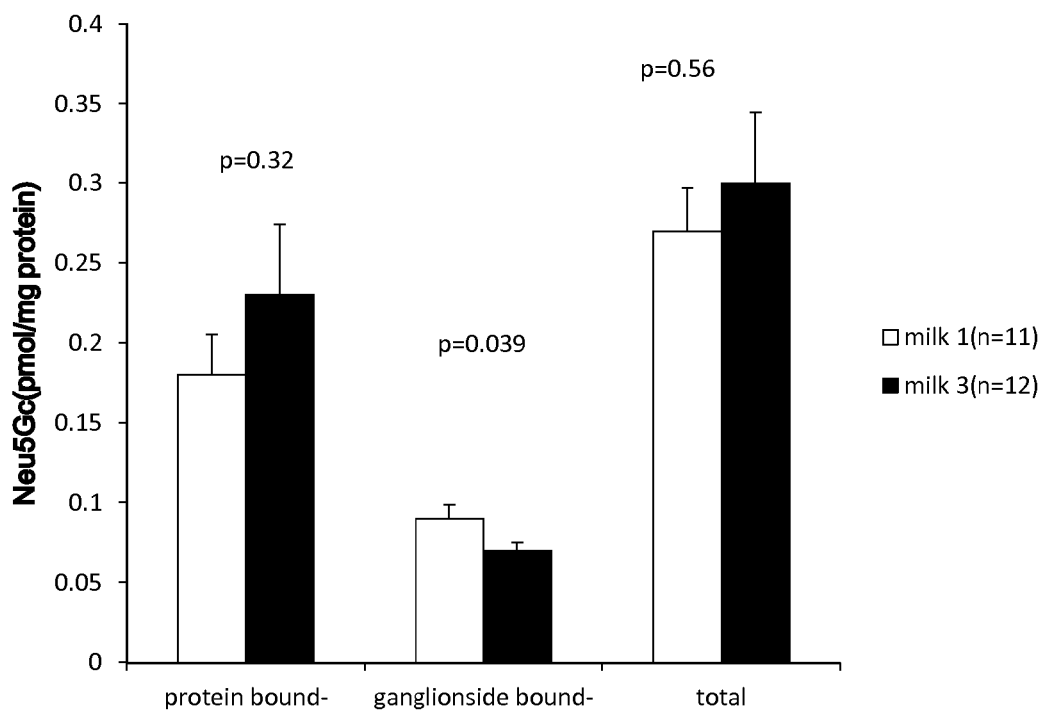

Based on the time interval between the trials, piglet's short-term memory (STM) and long-term memory (LTM) were evaluated. The time interval between trials of less than 5 min and more than 5 min was defined as STM and LTM, respectively. As a result, dietary sialyllactose supplementation (Milk 3) was shown to significantly improve STM and LTM in the easy and difficult task ($P<0.05$, One-way ANOVA, FIG. 6A and FIG. 6B)

Conclusion

The above results demonstrate that a dietary supplementation with a combination of 3'-Sialyllactose and 6'-Sialyllactose, especially in the inventive weight ratio of 4.4:1, significantly improves learning performance, short-term memory (STM) and long-term memory (LTM) in the developing piglets. Further, it was shown that sialic acid in oligosaccharide bound form (sialyllactose) is more effective in improving learning performance and enhancing short-term memory (STM) and long-term memory (LTM) function in piglets than sialic acid in protein-bound form (sialyl core 1). Furthermore, it was demonstrated that a combination of 3'-Sialyllactose and 6'-Sialyllactose as present in human breast milk is more effective in improving learning performance and enhancing short-term memory (STM) and long-term memory (LTM) than 3'-sialyllactose, even if the latter is combined with sialic acid in protein-bound form (sialyl core 1) and lactoferrin.

Example 4: Sialic Acid Concentration in Brain Frontal Cortex and Hippocampus

To determine whether dietary sialic acid supplementation could increase sialic acid content in the brain, the concentration and distribution of the sialic acid family members N-acetylneuraminic acid (Neu5Ac), N-glycolylneuraminic acids (Neu5Gc) and ketodeoxynonulosonic acid (KDN) were analyzed in brain hippocampus and frontal cortex of the control group (milk 1) and of the sialyllactose group (milk 3) of Example 2.

Method

Ganglioside-bound and protein-bound sialic acids were analyzed separately using a common method as published by Wang et al., *Sialic acid concentration of brain gangliosides: Variation among eight mammalian species.* Comp Biochem Phys 119A, 1998; 1:435-439; or Wang et al., *Brain ganglioside and glycoprotein sialic acid in infants fed human milk vs infant formula.* Am J Clin Nutr 2003; 78:1024-9. Briefly, brain frontal cortex and hippocampus (50 mg) of the piglets of Example 2 were homogenized with 150 μL distilled water and added to 525 μL methanol with constant shaking. Chloroform (270 μL) was added, the mixture was centrifuged (2000*g, 30 min, 4° C.) and the supernatant was removed. The brain residue was re-extracted with 100 μL water and 400 μL chloroform:methanol (1:2 vol/vol), and centrifuged at 3000*g, for 30 min, at 4° C. The two brain extracts were combined, 313 μL water was added to give a chloroform:methanol:water value (~tissue) of 1:2:1.4, and then the mixture was centrifuged (3000*g, 10 min, 4° C.). The upper phase was set aside while 150 μL methanol and 100 μL of 0.01 mol KCl were added slowly to the lower phase and mixed for 2 min and then centrifuged (3000*g, 15 min, 4° C.). The two upper phases were combined, and 1-butanol (10 μL) was added to prevent foaming. The mixture was then evaporated and freeze-dried. The dried material was re-dissolved in 200 μL chloroform:methanol (1:1, vol/vol), and sonicated. Ganglioside and protein bound sialic acid were released by hydrolysis sample with 0.1M trifluoracetic acid and 0.05M $H_2SO_4$ at 80° C. for 150 min and 60 min, respectively. Sialic acid concentrations in both ganglioside and protein fractions were determined by using HPLC-MS/MS.

Results

Ganglioside-bound Neu5Ac and total Neu5Ac in hippocampus and frontal cortex were significantly higher in the sialyllactose group as compared with the control group (see FIG. 7A-D). Neu5AC is the predominant form of sialic acid in the brain (FIG. 7A and FIG. 7C) and Neu5Gc only took about 0.01% in hippocampus and 0.1% in frontal cortex of total sialic acid in the brain (FIG. 7B and FIG. 7D), KDN was not detected in both hippocampus and frontal cortex.

Example 5: In Vivo Brain Structural Analysis Using Magnetic Resonance Imaging (MRI) Technique Differences of Fractional anisotropy (FA) were measured in the corpus callosum (white matter fiber tract) by non-invasive MRI between the sialyllactose group (Milk 3) and the control group (Milk 1) of Example 2. Corpus callosum was divided into three regions of genu, body and splenium. Using DTI Studio software (http://dsi-studio.labsolver.org), the region of interest (ROI) was placed to the brighter of those regions at sagittal plane of CC, the ROI size of genu, body and splenium was about 4-6 voxel, 6-8 voxel and 4-6 voxel, respectively.

VBM Analysis of Grey Matter and White Matter Between the Groups

The data of brain MRI scanning was normalized, segmented, smoothed and subjected to statistical data analysis. Briefly the individual pig MRI was registered into the standard space, and manually aligned to whole brain template (Tf) that we have made in SPM8 Display module (Wellcome Trust Centre for Neuroimaging, UCL Institute of Neurology, London, UK). The origin (0,0,0) was set on the bottom part of the bend of the posterior commissure (PC) in the midsagittal plan, and the left, posterior, inferior orientation matched to the whole brain template. Then, the aligned images were normalized to the whole brain template with no affine regularization because of large individual variance across piglets, with voxel sizes remained 0.5×0.5×1, bounding box (a three-dimensional space) encompassed the following x, y, z dimensions (−35, 35; −60, 50; −20, 40). All normalized images were segmented into grey matter (GM), white matter (WM), and cerebrospinal fluid (CSF) with tissue probability maps that we have made (Pf). "Segment" Tool within SPM8 divided images of all brains into GM, WM and CSF images with a mixture of Gaussian algorithm (Ashburner and Friston, 2005). A Gaussian smoothing kernel of 2 mm were applied and statistically analysed: Two-sample t-test; the covariate is whole brain volume.

Results

As displayed in Table 3, a significantly larger grey matter volume was found in the sialyllactose group (Milk 3) as compared to the control group (Milk 1) in the region of Insular cortex, Somatosensory cortex, Parahippocampal, Superior temporal, and Cerebellar lobule. Table 3 shows regions of significantly different grey matter volume for the sialyllactose group (Milk 3) relative to the control group (Milk 1).

TABLE 3

| Region | Laterality | Cluster Size | P | T | MNI Coordinate | | |
|---|---|---|---|---|---|---|---|
| | | | | | X | Y | Z |
| Insular cortex | L | 20 | 0.005 | 3.403 | −15 | 21 | 2 |
| Somatosensory cortex | L | 69 | 0.005 | 4.6852 | −13 | 8 | 22 |

TABLE 3-continued

| Region | Laterality | Cluster Size | P | T | MNI Coordinate X | Y | Z |
|---|---|---|---|---|---|---|---|
| Parahippocampal | L | 33 | 0.005 | 3.5598 | −18 | 5 | −5 |
| Superior temporal | L | 40 | 0.005 | 4.1789 | −22 | −5 | 14 |
| Cerebellar lobule | R | 28 | 0.005 | 3.5109 | 6 | −16 | 2 |

Conclusion

The somatosensory cortex is an area of the brain that processes input from the various systems in the body that are sensitive to touch. The brain insular cortex is a portion of the cerebral cortex folded deep within the lateral sulcus that is involved in functions of perception, motor control, self-awareness, cognitive functioning, and interpersonal experience. Thus, the combination of 3'-Sialyllactose and 6'-Sialyllactose, especially in the inventive weight ratio of 4.4:1 was also shown to significantly enhance functions of perception, motor control, self-awareness, cognitive functioning and/or interpersonal experience in an individual.

Example 6: Clinical Trial on 3'-Sialyllactose/6'-Sialyllactose Ratio in Breast Milk of Healthy Mothers Study Design An open, single-centre, 1 group study was conducted including 50 subjects (mothers) lasting 8 months. Only healthy volunteers were included.

All subjects complied with all the following inclusion criteria: 1. Gestational age between 37 and not above 42 weeks, 2. Baby to be enrolled between birth and V1, 3. Mother not younger than 18 years and not older than 40 years of age, 4. pre-pregnancy BMI of the mother between 18.5-29. 5. Mothers willing to breastfeed for the first 8 months after giving birth.

Subjects representing one or more of the following criteria are excluded from participation in the study: 1. Gestational diabetes, 2. HTA>140/90, 3. Mothers who are smokers while breast-feeding, 4. Subject who cannot be expected to comply with the study procedures. 5. Currently participating or having participated in another clinical trial during the last 12 weeks prior to the beginning of this study.

SL Sample Preparation and Analysis

Sialyllactose (SL) analysis was conducted in duplicates on a 1 mL sample of whole breast milk, corresponding to a complete feed, and taken after 11, 30, 60, 120 and 240 days after infants' birth (post partum).

Sample Preparation 1 mL of well mixed whole breast milk was centrifuged for 20 min at 1700×g. About 0.1 mL of skimmed milk supernatant was diluted 10× with water and 0.01 mL of the thus diluted supernatant were taken as a sample for analysis.

Analysis

Samples were analysed by high performance ion exchange chromatography (HPAEC; Thermo, Dionex, Ca) equipped with a CarboPac PA1 column (Thermo, Dionex, Ca) for separation and a pulsed amperometric detector (PAD) for detection of carbohydrates. 3'-Sialyllactose and 6'-Sialyllactose identification was done based on comparison of retention times to authentic standards. 3'-Sialyllactose and 6'-Sialyllactose were quantified using external standard curves with pure authentic 3'-Sialyllactose and 6'-Sialyllactose, respectively, and the weight ratio of 3'-Sialyllactose and 6'-Sialyllactose was calculated.

Results

As a result it was found that the weight ratio of 3'-Sialyllactose and 6'-Sialyllactose in human breast milk increases with time as determined after 11, 30, 60,120 and 240 days after infants' birth. While at the very beginning of the lactation period the 3'SL/6'SL ratio is about 1.53:10 with 6'SL as the major portion of sialyllactose in human breast milk, said ratio shifts with time towards about 5.86:1 with 3'SL as the major portion of sialyllactose in human breast milk after 8 months post partum. Further, the mean weight ratio of 3'-Sialyllactose and 6'-Sialyllactose in human breast milk during the lactation period was found to be about 1:1.

Conclusion

Example 6 clearly demonstrates that the nutritional composition of the present invention provides 3'-Sialyllactose and 6'-Sialyllactose in ranges matching the mother's milk physiological levels over time.

Summary

The above results demonstrate that sialyllactose supplementation according to the invention significantly enhances the learning speed, short-term memory and long-term memory in individuals. It was also shown for the first time that such sialyllactose supplementation significantly increased the sialic acid (Neu5Ac) concentration in brain hippocampus and frontal cortex in individuals. A summary of these results is given in FIG. 8.

Moreover, results of in vivo MRI further showed that dietary sialyllactose significantly increased grey matter volume of many important brain regions in all treatment group compared with their control group.

In sum, the results significantly support the benefits of dietary sialyllactose as essential nutrient for early neurodevelopment and cognitive function in piglets as an animal model of human infants.

Having thus described the present invention in detail and the advantages thereof, it is to be understood that the detailed description is not intended to limit the scope of the invention thereof.

The invention claimed is:

1. A method for enhancing learning skills and/or enhancing memory function in an individual in need thereof by increasing the sialic acid concentration in the brain of the individual, the method comprising administering a nutritional composition comprising 3'-Sialyllactose (3'-SL) and 6'-Sialyllactose (6'-SL) in a weight ratio between 10:1 and 1:10 to the individual,
   wherein the individual has at least one characteristic selected from the group consisting of preterm, small for gestational age (SGA), and low birth weight (LBW),
   the nutritional composition does not contain N-acetylated oligosaccharide,
   the 3'-Sialyllactose (3'-SL) and the 6'-Sialyllactose (6'-SL) are administered to the individual during the first two weeks after birth in an amount comprising from 150 mg to 170 mg of total sialyllactose per kg body weight per day and/or from 450 mg to 530 mg of N-Acetyl-neuraminic acid (Neu5Ac) per kg body weight per day; and
   the 3'-Sialyllactose (3'-SL) and the 6'-Sialyllactose (6'-SL) are administered to the individual from the first two weeks after birth up to 2 months after birth in an amount comprising from 120 mg to 140 mg of total sialyllactose per kg body weight per day and/or from 350 mg to 430 mg of Neu5Ac per kg body weight per day.

2. The method according to claim 1, wherein the 3'-Sialyllactose (3'-SL) and the 6'-Sialyllactose (6'-SL) are in a weight ratio between 10:1 and 2:1.

3. The method according to claim 1, wherein the 3' Sialyllactose (3'-SL) and the 6'-Sialyllactose (6'-SL) are in an amount of from 50 mg to 2500 mg of total sialyllactose per L of the nutritional composition.

4. The method according to claim 1, wherein the increasing the sialic acid concentration in the brain of the individual comprises increasing the sialic acid concentration in a brain region selected from the group consisting of hippocampus, frontal cortex, and a combination thereof.

5. The method according to claim 1, wherein the enhancing memory function of the individual comprises enhancing both short-term memory function and long-term memory function.

6. The method according to claim 1, wherein the individual is a mammal.

7. The method according to claim 1, wherein the nutritional composition is in a form selected from the group consisting of an infant formula, a starter infant formula, a preterm infant formula, a fortifier, a human milk fortifier, a baby food formula, a medical food product for clinical nutrition, and a supplement suitable for administering during the first two weeks after birth.

8. The method according to claim 1, wherein the 3'-Sialyllactose (3'-SL) and the 6'-Sialyllactose (6'-SL) are administered to the individual during the first two weeks after birth in an amount comprising from 160 mg to 165 mg of total sialyllactose per kg body weight per day.

9. The method according to claim 1, wherein the 3'-Sialyllactose (3'-SL) and the 6'-Sialyllactose (6'-SL) are administered to the individual during the first two weeks after birth in an amount comprising 162 mg of total sialyllactose per kg body weight per day.

10. The method according to claim 1, wherein the 3'-Sialyllactose (3'-SL) and the 6'-Sialyllactose (6'-SL) are administered to the individual during the first two weeks after birth in an amount comprising from 450 mg to 500 mg of N-Acetyl-neuraminic acid (Neu5Ac) per kg body weight per day.

11. The method according to claim 1, wherein the 3'-Sialyllactose (3'-SL) and the 6'-Sialyllactose (6'-SL) are administered to the individual from the first two weeks after birth up to 2 months after birth in an amount comprising from 390 mg to 430 mg of N-Acetyl-neuraminic acid (Neu5Ac) per kg body weight per day.

12. The method according to claim 1, wherein the nutritional composition comprises the 3'-Sialyllactose (3'-SL) and the 6'-Sialyllactose (6'-SL) in a weight ratio of 4.4:1.

13. The method according to claim 1, wherein the nutritional composition comprises the 3'-Sialyllactose (3'-SL) and the 6'-Sialyllactose (6'-SL) in a weight ratio of 1:1.

14. The method according to claim 1, comprising making the nutritional composition by adding a supplement to human breast milk from the mother of the individual, the supplement comprising an ingredient selected from the group consisting of a preterm infant formula, a human milk fortifier, a preterm infant supplement, a protective hydrocolloid, a binder, a film forming agent, an encapsulating agent, a wall/shell material, a matrix compound, a coating, an emulsifier, surface active agent, a solubilizing agent, an adsorbent, a carrier, a filler, a co-compound, a dispersing agent, a wetting agent, a processing aid, a flowing agent, a taste masking agent, a weighting agent, a jellifying agent, a gel forming agent, water, gelatin, vegetable gum, ligninsulfonate, talc, sugar, starch, gum arabic, vegetable oil, polyalkylene glycol, a flavoring agent, a preservative, a stabilizer, an emulsifying agent, a buffer, a lubricant, a colorant, and mixtures thereof.

15. The method according to claim 1, wherein the nutritional composition further comprises a protein source in an amount of 1.8 to 2.0 g/100 kcal of the composition.

16. The method according to claim 1, wherein the nutritional composition further comprises a protein source in an amount of 1.4 to 1.7 g/100 kcal of the composition.

* * * * *